(12) United States Patent
Pittner et al.

(10) Patent No.: US 8,273,713 B2
(45) Date of Patent: Sep. 25, 2012

(54) METHODS OF TREATING OBESITY USING PYY[3-36]

(75) Inventors: Richard A. Pittner, San Diego, CA (US); Andrew A. Young, La Jolla, CA (US); James R. Paterniti, Jr., San Diego, CA (US)

(73) Assignee: Amylin Pharmaceuticals, LLC, San Diego, CA (US)

(*) Notice: Subject to any disclaimer, the term of this patent is extended or adjusted under 35 U.S.C. 154(b) by 668 days.

(21) Appl. No.: 10/016,969

(22) Filed: Dec. 14, 2001

(65) Prior Publication Data

US 2002/0141985 A1 Oct. 3, 2002

Related U.S. Application Data

(60) Provisional application No. 60/256,216, filed on Dec. 14, 2000.

(51) Int. Cl.
*A61K 38/22* (2006.01)
*C07K 14/575* (2006.01)
(52) U.S. Cl. .......................... 514/12; 530/300
(58) Field of Classification Search .............. 424/198.1; 514/12, 21
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,701,441 A | 10/1987 | Kaira |
| 4,839,343 A | 6/1989 | Waeber et al. |
| 4,891,357 A | 1/1990 | Kala |
| 4,892,538 A | 1/1990 | Aebisher et al. |
| 5,459,039 A | 10/1995 | Modrich et al. |
| 5,498,531 A | 3/1996 | Jarrell |
| 5,574,010 A | 11/1996 | McFadden |
| 5,604,203 A | 2/1997 | Balasubramaniam |
| 5,696,093 A | 12/1997 | Tseng |
| 5,824,778 A | 10/1998 | Ishikawa et al. |
| 5,824,784 A | 10/1998 | Kinstler et al. |
| 5,912,227 A | 6/1999 | Croom, Jr. et al. |
| 5,939,462 A | 8/1999 | Connell et al. |
| 5,968,819 A | 10/1999 | Gerald et al. |
| 5,980,945 A | 11/1999 | Ruiz |
| 6,013,622 A | 1/2000 | Bruno et al. |
| 6,315,203 B1 | 11/2001 | Ikeda et al. |
| 6,355,478 B1 | 3/2002 | Baez et al. |
| 6,391,343 B1 | 5/2002 | Yen |
| 6,420,532 B1 | 7/2002 | Gerald et al. |
| 6,558,708 B1 | 5/2003 | Lin |
| 6,569,832 B1 | 5/2003 | Knudsen et al. |
| 6,734,166 B1 | 5/2004 | Croom, Jr. et al. |
| 2002/0094346 A1 | 7/2002 | Lin |
| 2003/0129176 A1* | 7/2003 | Jones et al. ............... 424/94.1 |
| 2003/0224983 A1 | 12/2003 | Nielsen |
| 2004/0228846 A1 | 11/2004 | Pang et al. |

FOREIGN PATENT DOCUMENTS

| | | |
|---|---|---|
| EP | 0 992 239 A | 4/2000 |
| WO | WO 83/04053 | 11/1983 |
| WO | WO 89/01967 | 3/1989 |
| WO | WO 90/02580 | 3/1990 |
| WO | WO 90/15637 | 12/1990 |
| WO | WO 91/10425 | 7/1991 |
| WO | WO 91/10470 | 7/1991 |
| WO | WO 94/16101 | 7/1994 |
| WO | 98/30231 A1 | 7/1998 |
| WO | WO 99/07404 | 2/1999 |
| WO | WO 99 15516 | 4/1999 |
| WO | WO 99/25727 | 5/1999 |
| WO | WO 99/25728 | 5/1999 |
| WO | 99/40928 A1 | 8/1999 |
| WO | WO 00/47219 | 8/2000 |
| WO | WO 00 68197 | 11/2000 |
| WO | WO 01 62737 | 8/2001 |
| WO | WO 01 76631 | 10/2001 |
| WO | WO 03/026591 A2 | 4/2003 |
| WO | WO 03/057235 | 5/2003 |
| WO | WO 03/105763 | 12/2003 |

OTHER PUBLICATIONS

Naslund et al., Energy intake and appetite are suppressed by glucagon-like peptide-1 (GLP-1) in obese men. Int. J. Obes. Relat. Metab. Disord. 23:304-311, 1999.*
Morley et al., An investigation of tolerance to the actions of leptogenic and anorexigenic drugs in mice. Life Sci. 41:2157-2165, 1987.*
Russell Ross, Atherosclerosis—an inflammatory disease. N. Engl. J. Med 340:115-126, 1999.*
Adrian T. E., et al. "Human distribution and release of a putative new gut hormone, peptide YY." *Gastroenterology* 89:1070-7, 1985.
Asakawa A., et al. "Mouse pancreatic polypeptide modulates food intake, while not influencing anxiety in mice." *Peptides* 20: 1445-8, 1999.
Balasubramaniam A., et al. "Structure-activity studies including a $\Psi(CH_2)$-NH) scan of peptide YY (PYY) active site, PYY(22-36), for interaction with rat intestinal PYY receptors: development of analogues with potent in vivo activity in the intestine." *J Med Chem* 43:3420-7, 2000.
Bonaz B., et al. "Peripheral peptide YY induces c-fos-like immunoreactivity in the rat brain." *Neurosci Lett* 163:77-80, 1993.
Brown K. K., et al. "A Novel N-Aryl Tyrosine Activator of Peroxisome Proliferator-Activated Receptor-Gamma Reverses the Diabetic Phenotype of the Zucker Diabetic Fatty Rat." *Diabetes* 48: 1415-24, 1999.
Campfield L. A., et al. "Recombinant mouse OB protein: Evidence for a peripheral signal linking adiposity and central neural networks." *Science* 269:546-549, 1995.
Chen C. H., et al. "Central inhibitory action of peptide YY on gastric motility in rats." *Am J Physiol* 269: R787-R792, 1995.
Chen C. H., et al. "Intracisternal injection of peptide YY inhibits gastric emptying in rats." *Regul Pept* 61:95-98, 1996.
Chen C. H., et al. "PYY and NPY: control of gastric motility via action on Y1 and Y2 receptors in the DVC." *Neurogastroenterol Motil* 9:109-116, 1997.

(Continued)

*Primary Examiner* — Ruixiang Li

(57) ABSTRACT

Methods and compositions are disclosed to treat metabolic disorders such as obesity, diabetes, and increased cardiovascular risk comprising administering a therapeutically effective amount of a PYY or a PYY agonist.

7 Claims, 8 Drawing Sheets

OTHER PUBLICATIONS

Clark J. T., et al. "Neuropeptide Y and human pancreatic polypeptide stimulate feeding behavior in rats." *Endocrinology* 115:427-9, 1984.
Clark J. T., et al. "Neuropeptide Y (NPY)-induced feeding behavior in female rats: comparison with human NPY ([Met17]NPY), NPY analog ([norLeu4]NPY) and peptide YY." *Regul Pept* 17:31-9, 1987.
Corp E. S., et al. "Effect of fourth ventricular neuropeptide Y and peptide YY on ingestive and other behaviors." *Am J Physiol* 259:R317-23, 1990.
Deng X., et al. "PYY potently inhibits pancreatic exocrine secretion mediated through CCK-secretin-stimulated pathways but not 2-DG-stimulated pathways in awake rats." *Dig Dis Sci* 46:156-65, 2001.
Eberlein G. A., et al. "A new molecular form of PYY: structural characterization of human PYY(3-36) and PYY(1-36)." *Peptides* 10:797-803, 1989.
Gedulin B., et al. "Assessment of gastric emptying from appearance in plasma of 3H from gavaged [3-3H] glucose in conscious rats: effects of amylin." *Gastroenterology* 108:A604, 1995.
Gehlert D. R. "Multiple receptors for the pancreatic polypeptide (PP-fold) family: physiological implications." *Proc Soc Exp Biol Med* 218:7-22, 1998.
Grandt D., et al. "Two molecular forms of peptide YY (PYY) are abundant in human blood: characterization of a radioimmunoassay recognizing PYY 1-36 and PYY 3-36." *Regul Pept* 51:151-9, 1994.
Greeley G. H. Jr., et al. "Inhibition of gastric acid secretion by peptide YY is independent of gastric somatostatin release in the rat." *Proc Soc Exp Biol Med* 189:325-8, 1988.
Guan D., et al. "Peptide-YY, a new partner in the negative feedback control of pancreatic secretion." *Endocrinology* 128:911-6, 1991.
Gue M et al. "Reversal by NPY, PYY and 3-36 molecular forms of NPY and PYY of intracisternal CRF-induced inhibition of gastric acid secretion in rats." *Br J Pharmacol* 118:237-42, 1996.
Halaas J. L., et al. "Weight-reducing effects of the plasma protein encoded by the obese gene." *Science* 269:543-6, 1995.
Haynes J. M., et al. "Neuropeptide Y (NPY) and peptide YY (PYY) effects in the epididymis of the guinea-pig: evidence of a pre-junctional PYY-selective receptor." *Br J Pharmacol* 122:1530-6, 1997.
Hoentjen F., et al. "Role of circulating peptide YY in the inhibition of gastric acid secretion by dietary fat in humans." *Scand J Gastroenterol* 35:166-71, 2000.
Iyengar S., et al. "Characterization of neuropeptide Y-induced feeding in mice: do Y1-Y6 receptor subtypes mediate feeding?" *J Pharmacol Exp Ther* 289:1031-40, 1999.
Kanatani A., et al. "Role of the Y1 receptor in the regulation of neuropeptide Y-mediated feeding: comparison of wild-type, Y1 receptor-deficient, and Y5 receptor-deficient mice." *Endocrinology* 141:1011-6, 2000.
Kato K., et al. "CGRP antagonists enhance gastric acid secretion in 2-h pylorus-ligated rats." *Peptides* 16:1257-1262, 1995.
Kawakubo K., et al. "Intracisternal PYY inhibits gastric lesions induced by ethanol in rats: role of PYY-preferring receptors?" *Brain Res* 854:30-4, 2000.
Kimmel J. R., et al. "Isolation and characterization of chicken insulin." *Endocrinology* 83: 1323-30, 1968.
Kopelman P. G. "Obesity as a medical problem." *Nature* 404: 635-43, 2000.
Lloyd K. C. K., et al. "Inhibitory effect of PYY on vagally stimulated acid secretion is mediated predominantly by Y-1 receptors." *Am J Physiol* 270:G123-G127, 1996.
Malaisse-Lagae F., et al. "Pancreatic polypeptide: a possible role in the regulation of food intake in the mouse." Hypothesis. *Experientia* 33: 915-7, 1977.
Marsh D. J., et al. "Role of the Y5 neuropeptide Y receptor in feeding and obesity." *Nat Med* 4:718-21, 1998.
Michel M. C., et al. "XVI. International Union of Pharmacology recommendations for the nomenclature of neuropeptide Y, peptide YY, and pancreatic polypeptide receptors." *Pharmacol Rev* 50: 143-50, 1998.
Morley J. E., et al. "Modulation of food intake by peripherally administered amylin." *Am J Physiol* 267:R178-R184, 1994.
Morley J. E., et al. "Peptide YY (PYY), a potent orexigenic agent." *Brain Res* 341: 200-203, 1985.
Munson P. J. et al. "Ligand: a versatile computerized approach for characterization of ligand-binding systems." *Anal Biochem* 107: 220-39, 1980.
Nakajima M., et al. "Effects of pancreatic polypeptide family peptides on feeding and learning behavior in mice." *J Pharmacol Exp Ther* 268:1010-4, 1994.
Pappas T. N., et al. "Peptide YY release by fatty acids is sufficient to inhibit gastric emptying in dogs." *Gastroenterology* 91:1386-9, 1986.
Pappas T. N., et al. "Peptide YY inhibits meal-stimulated pancreatic and gastric secretion." *Am J Physiol* 248:G118-23, 1985.
Pelleymounter M. A., et al. "Effects of the obese gene product on body weight regulation in ob/ob mice." *Science* 269:540-543, 1995.
Rissanen A., et al. "Risk of disability and mortality due to overweight in a Finnish population." *BMJ* 301: 835-7, 1990.
Savage A. P., et al. "Effects of peptide YY (PYY) on mouth to caecum intestinal transit time and on the rate of gastric emptying in healthy volunteers." *Gut* 28:166-70, 1987.
Scatchard G. "The attraction of proteins for small molecules and ions." *Ann NY Acad Sci* 51: 660, 1949.
Schwartz M. W., et al. "Central nervous system control of food intake." *Nature* 404: 661-71, 2000.
Stanley B. G., et al. "Paraventricular nucleus injections of peptide YY and neuropeptide Y preferentially enhance carbohydrate ingestion." *Peptides* 6: 1205-11, 1985.
Surwit R. S., et al. "Differential effects of fat and sucrose on the development of obesity and diabetes in C57BL/6J and A/J mice." *Metabolism—Clinical and Experimental* 44:645-651, 1995.
Taniguchi H., et al. "Pharmacological profile of T-0632, a novel potent and selective CCKA receptor antagonist, in vivo." *Eur J Pharmacol* 312: 227-33, 1996.
Tatemoto K. "Isolation and characterization of peptide YY (PYY), a candidate gut hormone that inhibits pancreatic exocrine secretion." *Proc Natl Acad Sci U S A* 79: 2514-8, 1982.
Tatemoto K. "Neuropeptide Y: complete amino acid sequence of the brain peptide." *Proc Natl Acad Sci U S A* 79: 5485-9, 1982.
Tatemoto K., et al. "Neuropeptide Y a novel brain peptide with structural similarities to peptide YY and pancreatic polypeptide." *Nature* 296: 659-60, 1982.
Ueno N., et al. "Decreased food intake and body weight in pancreatic polypeptide-overexpressing mice." *Gastroenterology* 117: 1427-32, 1999.
Yang H., et al. "PYY-preferring receptor in the dorsal vagal complex and its involvement in PYY stimulation of gastric acid secretion in rats." *Br J Pharmacol* 123: 1549-54, 1998.
Yang H., et al. "PYY in brain stem nuclei induces vagal stimulation of gastric acid secretion in rats." *Am J Physiol* 268: G943-8, 1995.
Yoshinaga K., et al. "Structural requirements of peptide YY for biological activity at enteric sites." *Am J Physiol* 263:G695-701, 1992.
Young A., et al. "Genetically obese (ob/ob) mice are more sensitive to amylin and endotoxin-induced suppression of food intake." *Program and Abstracts, 10th International Congress of Endocrinology* 419 (poster p2-58), 1996.
Kushi, et al., "Obesity and mild hyperinsulinemia found in Neuropeptide Y-Y1 receptor-deficient mice." *Proc. Natl. Acad. Sci. USA* vol. 95, pp. 15659-15664, Dec. 1998.
Allen, et al., "Effects of Peptide YY and Neuropeptide Y on Gastric Emptying in Man." *Digestion* 30:255-262, 1984.
Hagan, M.M. et al. "Effect of Naloxone and Antidepressants on Hyperphagia Produced by Peptide YY" *Pharmacology Biochemistry and Behavior*, 45(4): 941-944 (1993).
Widdowson P.S. et al. "Distribution of (Leu31, Pro34)NPY-sensitive, BIBP3226-insensitive (125I)PYY(3-36) binding sites in rat brain: Possible relationship to Y5 NPY receptors", *Brain Research* 778(1): 242-250 (1997).
Derwent Search: Class B02, AN 1999-254678 XP002201834.
Zai et al., "Effect of peptide YY on gastric motor and secretory activity in vagally innervated and denervated corpus pouch dogs", *Regulatory Peptides*, vol. 61, pp. 181-188 (1996).
Wiley et al., "Mechanism of Action of Peptide YY to Inhibit Gastric Motility", *Gastroenterology*, vol. 100, pp. 865-872 (1991).

Okada et al., "Peripherally not Centrally Administered Peptide YY(PYY) Decreases High Fat Diet Intake", The Endocrine Society 75th Annual Meeting Program & Abstracts, p. 180, Abstract 520B (1993).
Batterham et al. "Inhibition of Food Intake in Obese Subjects by Peptide YY$_{3-36}$," N Engl J Med 2003 349:941-8.
Batterham et al. "Gut hormone PYY$_{3-36}$ physiologically inhibits food intake," Nature 2002 418:650-4.
Garlicki et al. "Cholecystokinin receptors and vagal nerves in control of food intake in rats," Amer Physiol Soc 1990.
Gomez et al. "Intestinal peptide YY: ontogeny of gene expression in rat bowel and tropic actions on rat and mouse bowel," Amer Physiol Soc 1995.
Iyengar et al. "Characterization of Neuropeptide Y-Induced Feeding in Mice: Do Y1-Y6 Receptor Subtypes Mediate Feeding?" J Pharm and Exp Therap. 1999 289(2):1031-40.
Morley, "An Approach to the Development of Drugs for Appetite Disorders," Neuropscholiology 1989 21:22-30.
Morley, et al., "An Investigation of Tolerance to the Actions of Leptogenic and Anorexigenic Drugs in Mice," Life Sciences, 1987 41:2257-2165.
Morley et al. "Peptide YY (PYY), a potent orexigenic agent," Brain Research 1985 341:200-3.
Chen et al. "Sensitive Radioimmunoassay for Measurement of Circulating Peptide YY" *Gastroenterology* 87:1332-1338, 1984.
Grandt et al. "Novel Generation of Hormone Receptor Specificity by Amino Terminal Processing of Peptide YY" *Biochemical and Biophysical Research Comm* vol. 186, No. 3:1299-1306, 1992.
Leibowitz et al. "Analysis of Neuropeptide Y-Induced Feeding: Dissociation of Y$_1$ and Y$_2$ Receptor Effects on Natural Meal Patterns" *Peptides* 12: 1251-1260, 1991.
Medeiros et al "Processing and Metabolism of Peptide-YY: Pivotal Roles of Dipeptidylpeptidase-IV, Aminopeptidase-P, and Endopeptidase-24.11" *Endocrinology* vol. 134, No. 8: 2088-2094, 1994.
Tatemoto et al. "Isolation and Primary Structure of Human Peptide YY" *Biochemical and Biophysical Res. Comm.* vol. 157, No. 2: 713-717, 1988.
The Small Encyclopedia, Moscow, Meditsina Publishers, 1996 vol. 4, pp. 59-62, the article on "Obesity".
Towfigh et al., Surgical Forum vol. 50: 25-27 (1999).
Ahren, B. et al., Eur J Endocrinol 134, 362-365 (1996).
Aponte, G.W., et al., FASEB J 3, 1949-55 (1989).
Barany, F. Proc Natl Acad Sci U S A 88, 189-193 (1991).
Bartlett PA, et al., Bioorg Chem.14:356-377 (1986).
Berge, S.M., et al., J Pharm Sci 66, 1-19 (1977).
Bertrand, G., et al., Pancreas 7, 595-600 (1992).
Birdsall, N.J.M. et al., Trends Pharmacol Sci 4, 459-463 (1983).
Bottcher, G., et al., Pancreas 4, 282-288 (1989).
Bourguet E, et al., Bioorg Med Chem Lett.13:1561-1564 (2003).
Cook, D.L. et al., Nature 311, 271-273 (1984).
Coruzzi, G., et al., Arch Int Pharmacodyn Ther 302, 232-241 (1989).
Cotton, R.G. Mutat Res 285, 125-144 (1993).
Cotton, R.G., et al., Proc Natl Acad Sci U S A 85, 4397-4401 (1988).
Cox, H.M. et al., Br J Pharmacol 101, 247-252 (1990).
Dea, D., et al., Gastroenterology 96, 695-703 (1989).
Dox, I.G., et al., Definition of 'islet'. In: Anonymous The HarperCollins Illustrated Medical Dictionary, 1st edn. pp. 227 New York: HarperCollins Publishers, Inc.] (1993).
Dumont, Y., et al., Brain Res Mol Brain Res 26, 320-324 (1994).
Dumont Y, et al., Society for Neuroscience Abstracts. 1993;19:726. Abstract 299.8.
Ferber, S., et al., Journal of Biological Chemistry 269, 11523-11529 (1994).
Freshney, R.I. (Ed.) Culture of Animal Cells: A Manual of Basic Technique, pp. 4 New York: Alan R. Liss, Inc] (1983).
Gibbs, R.A., et al., Nucleic Acids Res 17, 2437-2448 (1989).
Gold, G., et al., Diabetes 30, 77-82 (1981).
Greeley, G.H. Jr, et al., Am J Physiol 254, E513-E517 (1988).
Grieco P, et al., Tetrahedron Lett.43:6297-6299 (2002).
Groth, C.G., et al., Transplant Proc 24, 972-973 (1992).

Grouzmann, E., et al., Endocrine Society Program & Abstracts 75th Annual Meeting, Las Vegas, NV, Jun. 9-12 180. Abstract 519B (1993).
Gu X, et al., Tetrahedron Lett. 44:5863-5866 (2003).
Hanessian S, et al., Tetrahedron 53:12789-12854 (1997).
Holliday, N.D. et al., Br J Pharmacol 119, 321-329 (1996).
Hsu, I.C., et al., Carcinogenesis 15, 1657-1662 (1994).
Hughes, S.D., et al., Proceedings of the National Academy of Sciences of the United States of America 89, 688-692 (1992).
Jackerott, M. et al, Endocrinology 138, 5013-5018 (1997).
Jackerott, M., et al., J Histochem Cytochem 44, 809-817 (1996).
Johnson, J.H., et al., Science 250, 546-549 (1990).
Jones, P.M. et al., Endocr Rev 19, 429-461 (1998).
Korsgren, O., et al., Transplantation 45, 509-514 (1988).
Krasinski, S.D., et al., Mol Endocrinol 5, 433-440 (1991).
Kumagai Braesch, M., et al., Transplant Proc 24, 679-680 (1992).
Lacy, P.E., et al., Science 254, 1782-1784 (1991).
Landegren, U., et al., Science 241, 1077-1080 (1988).
Liu, X.M., et al., Diabetes 40, 858-66 (1991).
Lluis, F., et al., Gastroenterology 94, 137-144 (1988).
Lundberg, J.M., et al., Proc Natl Acad Sci U S A 79, 4471-4475 (1982).
Lyznicki JM, et al., Am Fam Physician. 63:2185-2196 (2001).
Maxam, A.M. et al., Proc Natl Acad Sci U S A 74, 560-564 (1977).
Mazelin L, et al., J Auton Nerv Syst.73:38-45 (1998).
Morris GP, et al., Gastroenterology 96:795-803 (1989).
Mulder, H., et al., Microscopy Research and Technique 43, 313-321 (1998).
Myers, R.M., et al., Science 230, 1242-1246 (1985).
Myers, R.M., et al., Nature 313, 495-498 (1985).
Naeve, C.W., et al., Biotechniques 19, 448-453 (1995).
Nakazawa, H., et al., Proc Natl Acad Sci U S A 91, 360-364 (1994).
Ngo, J.T., et al., The protein folding problem and tertiary structure prediction, pp. 491-495. Boston: Birkhauser (1994).
Nieuwenhuizen, A.G., et al., Diabetologia 37, 871-878 (1994).
Odagiri, H., et al., J Biol Chem 271, 1909-1915 (1996).
Orita, M., et al., Proc Natl Acad Sci U S A 86, 2766-2770 (1989).
Otonkoski, T., et al., Diabetes 37, 286-291 (1988).
Randle, P.J. Diabetes Metab Rev 14, 263-283 (1998).
Rhodes, C.J. et al., J Cell Biol 105, 145-153 (1987).
Robbins, L.S., et al., Pathologic Basis of Disease, 3rd edn. pp. 972-990. Philadelphi: W. B. Saunders Company] (1984).
Saiki, R.K., et al., Nature 324, 163-166 (1986).
Saiki, R.K., et al., Proc Natl Acad Sci U S A 86, 6230-6234 (1989).
Saleeba, J.A. et al., Methods Enzymol 217, 286-295 (1993).
Sandberg M, et al., J Med Chem.41:2481-2491 (1998).
Sander, M., et al., Proc Natl Acad Sci U S A 95, 11572-11577 (1998).
Sanger, F., et al., Proc Natl Acad Sci U S A 74, 5463-5467 (1977).
Scheen, A.J. Drugs 54, 355-368 (1997).
Schuit, F.C. Horm Res 46, 99-106 (1996).
Simeonovic, C.J. et al., Aust J Exp Biol Med Sci 60 Pt 4, 383-390 (1982).
Souers AJ, et al., Tetrahedron 57:7431-7448 (2001).
Sullivan, S.J., et al., Science 252, 718-721 (1991).
Suzuki, T., et al., Gastroenterology 85, 114-121 (1983).
Thorens, B., et al., Proceedings of the National Academy of Sciences of the United States of America 87, 6492-6496 (1990).
Tsai JH, et al., Bioorg Med Chem 7:29-38 (1999).
Tuch, B.E., et al., J Endocrinol 132, 159-167 (1992).
Upchurch, B.H., et al., Development 120, 245-252 (1994).
Valera, A., et al., J Biol Chem 269, 28543-28546 (1994).
Verchere, C.B., et al, Endocrine Society Program & Abstracts 75th Annual Meeting, Las Vegas, NV, Jun. 9-12 180. Abstract 517B ., (1993).
Virgilio AA, et al., Tetrahedron 53:6635-6644 (1997).
Wahoff, D.C., et al., Transplant Proc 26, 804 (1994).
Wang, Z.L., et al., Endocrine Society Program & Abstracts 75th Annual Meeting, Las Vegas, NV, Jun. 9-12 180. Abstract 518B (1993).
Wells, J.A. Biochemistry 29, 8509-8517 (1990).
Wilson, J.D., et al., Diabetes 38 Suppl 1, 217-219 (1989).

On-Line Medical Dictionary. Dept. of Oncology, U of Newcastle. The Cancerweb Project (C)1997-2004 (defs of "hyperlipoproteinaemia" "hyperlipidemia" & "hyperlipidaemia".
Aponte, G.W. (2002) Peptides 23, 367-376.
Bousquet-Melou, A., et al., (1995) J Lipid Res 36, 451-461.
Karlsson, S. et al., (1996) Acta Physiologica Scandinavica 157, 305-306.
Pi-Sunyer, F.X. (2002) Obes Surg 12 Suppl 1, 6S-11S.
Slack, J.M. (1995) Development 121, 1569-1580.
St-Onge, M.P. et al., (2002) J Nutr 132, 329-332.
Tito, J.M., et al., (1993) Am J Surg 165, 690-696.
Valet, P., et al., (1990) J Clin Invest 85, 291-295.
Voisin, T., et al., (1993) J Biol Chem 268, 20547-20554.
Adrian TE, et al., "Lack of effect of pancreatic polypeptide in the rate of gastric emptying and gut hormone release during breakfast" Digestion. 1981 21:214-8.
Beltowski, J., et al., "What we know 10 years since its discovery?" Pol J Pharmaco. 2004;56:5-27.
Camilleri, M, et al., "Effects of vasoactive intestinal peptide and pancreatic polypeptide in rabbit intestine" Gut. 1981 22:14-8.
Cox, HM, et al., "The effecto neuropeptide Y and peptide YY on electrogenic ion transport in rate intestinal epithelia" J Physio. Apr. 1988;398:65-80.
Ebert, R., "Control of gastric empyting by regulatory peptides" Z Gastroenterol Verh. 1988 23:165-70.
Gustavsson S, et al., "Effects of vasoactive intestinal peptide and pancreatic polypeptide on small bowel propulsion in the rat" Gastroenterol. 1997 12:993-7.
Harding, RK, et al., "Identification and characterization of the emetic effects of peptide YY" Peptides 1989 10:24-4.
Kruger, DF, et al., "Clinical implication of amylin and amylin deficiency" Diabetes Educator 1999;25:389-398.
Martin, Jr, "The Y1 receptor subtype mediates the cardiovascular changes evoked by NPY administered into the posterior hypothalamic nucleus of conscious rat" Brain Res. 2004 1002:11-20.
Nightingale, JM, et al., "Gastrointestinal hormones in short bowel syndrome. Peptide YY may be the 'colonic brake' in gastric emptying" Gut. Aug. 1996;39(2):267-72.
Okumura, T, et at., "Intracisternal injection of pancreatic polypeptide stimulates gastric emptying in rates" Neurosci Lett. 1994 178(1):167-70.
Pheng, et al., "Agonist- and antagonis-induced sequestration/internalization of neuropeptide Y Y, receptors in HEK293 cells" British J of Pharma 2003 139:695-704.
Pironi, L, et al., "Fat-reduced ileal brake in humans: a dose-dependent phenomenon correlated to the plasma levels of peptide YY" Gastroenterology. 1993 105:733-9.
Sainsbury, A, et al., "Y4 receptor knockout rescues fertility in ob/ob mice" Genes Dev. 2002 16:1077-88.
Servin, AL, et al., "Peptide-YY and neuropeptide-Y inhibit vasoactive intestinal peptide-stimulated adenosine 3',5'-monophosphate production in rat small intestine: structural requirements of peptides for interacting with peptide-YY-preferring receptors". Endocrinology. Feb. 1989;124(2):692-700.
Taylor, IL, et al., "Effects of pancreatic polypeptide, caerulein, and bombesin on satiety in obese mice" Am J Physiol. 1985 248:G277-80.
Taylor, IL, "Role of peptide YY in the endocrine control of digestion" J Dairy Sci. 1993 76:2094-101.
Wager-Page, SA, et al., "Peripheral modulation of duodenal and colonic motility and arterial pressure by neuropeptide Y, neuropeptide Y fragment 13-36, peptide YY, and pancreatic polypeptide in rates: cholinergic mechanisms" Can J Physiol Pharmacol. 1993 71:768-75.
Wimalawansa, Amylin, Calcitonin Gene-related Peptide, Calcitonin, and Adrenomedullin: A Peptide Superfamily, Neurobiology, (2&3):167-239 (1997).
Young, AA, et al., "Dose-responses for the slowing of gastric emptying in a rodent model by glucagon-like peptide (7-36) NH2, amylin, cholecystokinin, and other possible regulators of nutrient uptake" Metabolism. 1996 45:1-3.
Ando, R. et al., Eur J Pharmacol. Sep. 7, 2001; 427(1):53-59.
Andres et al., Bioorganic & Medicinal Chemistry Letters 13(2003) 2883-2885.
Bader, R. et al., Biochemistry. 2002; 41(25):8031-8042.
Balasubramaniam, A. et al., Int J Pept Protein Res. Jan. 1987; 29(1):78-83.
Balasubramaniam, A. et al., Pept Res. Sep. 1988-Oct. 31, 1988; 1(1):32-35.
Balasubramaniam, A. et al., Peptides 14: 1011-1016 (1993).
Balasubramaniam, A., Peptides. 1997; 18(3):445-457.
Balasubramaniam et al., Peptides 23 (2002) 1485-1490.
Beck et al., FEBS 06785 244(1) 119-122 (1989).
Beck-Sickinger et al., J Recept Res 1993; 13(1-4) 215-228.
Berglund, M. et al., Exp Biol Med (Maywood). Mar. 2003; 228(3):217-244.
Bischoff, A., et al., Trends Pharmacol Sci. Mar. 1999; 20(3):104-106.
Boublik, J. H., et al., J Med Chem. Mar. 1989; 32(3):597-601.
Cabrele et al., Peptides 22(2001) 365-378.
Cabrele, C. et al., J Pept Sci. Mar. 2000; 6(3):97-122.
Cabrele, C. et al., J Biol Chem. 2000; 275(46): 36043-36048.
Cabrele, C. et al., Biochemistry. Jun. 25, 2002; 41(25):8043-8049.
Chen, Z. et al., FEBS Lett. Mar. 9, 2001; 492(1-2):119-122.
Conlon, J. M., Peptides. 2002; 23(2):269-278.
Corp, E. S. et al., Peptides. Mar. 2001; 22(3):493-499.
Cox, H. M. et al., Regul Pept. 1998; 75-76:3-8.
Dumont et al., EP J of Pharmacology, 238 (1993) 37-45.
Eto, B. et al., Peptides. 1995; 16(8):1403-1409.
Fackelmann USA Today, Health and Science Gut hormone could curb urge to overeat. (Aug. 7, 2002).
Feinstein et al., J. Med. Chem. 1992, 35, 2836-2843.
Fournier et al., Molecular Pharmacology, (1994) 45:93-101.
Gobbi et al., J. of Neurochemistry (1999) 72m 1663-1670.
Gordon et al., Neuroscience Letters, 119 (1990) 187-190.
Grundemar et al. Regulatory Peptides 62 (1996) 131-136.
Halatchev et al., Endocrinology 145(6) (2004) 2585-2590.
Henry et al., Obesity Research (Jan. 2005) 13(1): 36-47.
Hu et al., The J. of Biological Chemistry (Oct. 1996) 271(42): 26315-26319.
Inui, A., Trends Pharmacol Sci. Feb. 1999; 20(2):43-46.
Kanatani, A. et al., Biochem Biophys Res Commun. May 27, 2000; 272(1):169-173.
Kanatani, A. et al., Biochem Biophys Res Commun. Dec. 9, 1999; 266(1):88-91.
Keire, D. A. et al., Peptides. 2002; 23(2):305-321.
Keire, D. A. et al., Biochemistry. Aug. 15, 2000; 39(32):9935-9942.
Keire, D. A. et al., Am J Physiol. Jul. 2000; 279(1):G126-G131.
Kirby et al., J. Med. Chem. 1993; 36: 3802-3808.
Kirby et al., J. Med. Chem. 1995; 38: 4579-4586.
Krstenansky et al., Proc. Natl. Acad. Sci. USA Jun. 1989; 86: 4377-4381.
Krstenansky et al., Neuropeptides (1990) 17, 117-120.
Leban et al., J. Med. Chem. 1995, 38, 1150-1157.
Liu, C. D. et al., J Gastrointest Surg. Mar. 2001-Apr. 30, 2001; 5(2):147-152.
Lundell et al., JBC 270(49) 29123-29128 (1995).
Martin, N. M. et al., Int J Obes Relat Metab Disord. Jul. 2004; 28(7):886-893.
Mashiko et al., Endocrinology (2003) 144(5): 1793-1801.
Mullins, D. et al., Mol Pharmacol. 2001; 60(3):534-540.
Murakami, Y. et al., J Med Chem. Jul. 15, 1999; 42(14):2621-2632.
Murase et al., J Biochem (Tokyo) Jan. 1996 119(1): 37-41.
Parker, E. M. et al., Eur J Pharmacol. May 15, 1998; 349(1):97-105.
Parker, E. M. et al., Peptides. Mar. 2000; 21(3):393-399.
Parker et al., Can. J. Physiol. Pharmacol. (2000); 78: 150-161.
Potter et al., EP J. of Pharmacology 267 (1994) 253-262.
Renshaw, D. et al., Curr Drug Targets Mar. 2005; 6(2):171-179.
Rist et al., FEBS Letters 394 (1996) 169-173.
Rist et al., Eur. J. Biochem. (1997); 247: 1019-1028.
Sato, N. et al., J Med Chem. Feb. 27, 2003; 46(5):666-669.
Shan et al., Science (Sep. 27, 2002); 297: 2275-2279.
Sheikh, S. P. Am J Physiol. Nov. 1991; 261(5 Pt 1):G701-G715.
Silva, A. P. et al., Clin Chim Acta. Dec. 2002; 326(1-2):3-25.
Small, C. J., et al., Proc Natl Acad Sci U S A. Oct. 14, 1997; 94(21):11686-11691.

Soll et al. Eur. J. Biochem (2001); 268: 2828-2837.
Tatemoto, K. et al., Proc Natl Acad Sci U S A. Feb. 15, 1992; 89(4):1174-1178.
Thum, A. et al.; Exp Clin Endocrinol Diabetes. 2002; 110(3):113-118.
Totheroh, G., "Science Offers Promising Treatment for an Overweight Nation" CBN News (Sep. 4, 2003).
Tschop, M. et al., Nature. Jul. 8, 2004; 430(6996):1 p following 165; discussion 2 p following 165.
Tseng, W. W. et al., Peptides. 2002; 23(2):389-395.
Turnbull, A. V. et al., Diabetes. 2002; 51(8):2441-2449.
Walker, M. W. et al., Peptides. 1997;18(4):609-612.
Walker et al. The J of Neuroscience Jul. 1988, 8 (7): 2438-2446.
Weinberg, D. H. et al., J Biol Chem. Jul. 12, 1996; 271(28):16435-16438.
Wilding, J. P., Diabet Med. Aug. 2002; 19(8):619-627.
EP Patent Application No. 01991093.4 (EP Patent No. 1,349,563), Notice of Opposition by Glaxo Group Limited, filed Aug. 26, 2010, 47 pgs.
EP Patent Application No. 01991093.4 (EP Patent No. 1,349,563), Notice of Opposition by Novo Nordisk A/S, filed Sep. 1, 2010, 23 pgs.

Zukowska-Grojec, "Neuropeptide Y: Implications in vascular remodeling and novel therapeutics", DN&P 10(10):587 (1997).
Widdowson, "Regionally-selective down-regulation fo NPY receptor subtypes in the obese Zucker rat. Relationship to the y% 'feeding'receptor", Brain Res 758:17-25 (1997).
Thomson et al.," Small bowel review: Part II", Can J. Gastroenterol, 11(7):607 (1997).
Young et al., "Glucose-Lowering and insulin-sensitizing actions of Exendin-4; Studies in obese diabetec (ob/ob, db/db) mice, diabetic fatty Zucker rats, and diabetic rhesus", Diabetes 48:1026 (1999).
Mooradian & Thurman, "Drug therapy of postprandial hyperglycaemia", Drugs 57(1):19-29 (1999).
Kubitza et al., "Body weight has limited influence on the safety, tolerability, phan-nacokinetics, or phartriacociyriamics of rivaroxaban (BAY 59/7939) in healthy subjects", J. Clin. Pharmacol. 47;218 (2007).
Rogers & Hermann, "Peptide YY and neuropeptide Y: Reciprocal control fo digestion via modulation of the brain-got axis", Biomedical Ravimwo8:55-G9(1997).

* cited by examiner

METHODS OF TREATING OBESITY USING PYY[3-36]

CROSS-REFERENCE TO RELATED APPLICATION

This application claims priority to U.S. Provisional Application Ser. No. 60/256,216 entitled "Peptide YY and Peptide YY Agonists for Treatment of Obesity, Diabetes, and other Metabolic Disorders," filed Dec. 14, 2000, the contents of which are herein incorporated by reference.

FIELD OF THE INVENTION

The present invention relates to methods and compositions for treating metabolic conditions or disorders, particularly those which can be alleviated by reducing caloric availability, for example diabetes, obesity, eating disorders, insulin-resistance syndrome (Syndrome X), glucose intolerance, dyslipidemia, and cardiovascular disorders.

BACKGROUND

A number of related hormones make up the pancreatic polypeptide (PP) family. Pancreatic polypeptide was discovered as a contaminant of insulin extracts and was named more by its organ of origin, rather than functional importance (Kimmel, Pollock et al. *Endocrinology* 83: 1323-30, 1968). It is a 36-amino acid peptide [SEQ ID NO.: 1] containing distinctive structural motifs. A related peptide was subsequently discovered in extracts of intestine and named Peptide YY (PYY) because of the N- and C-terminal tyrosines (Tatemoto. *Proc Natl Acad Sci USA* 79: 2514-8, 1982) [SEQ ID NO.: 2]. A third related peptide was later found in extracts of brain and named Neuropeptide Y (NPY) (Tatemoto. *Proc Natl Acad Sci USA* 79: 5485-9, 1982; Tatemoto, Carlquist et al. *Nature* 296: 659-60, 1982) [SEQ ID NO.: 4].

These three related peptides have been reported to exert various biological effects. Effects of PP include inhibition of pancreatic secretion and relaxation of the gallbladder. Centrally administered PP produces modest increases in feeding that may be mediated by receptors localized to the hypothalamus and brainstem (reviewed by (Gehlert. *Proc Soc Exp Biol Med* 218: 7-22, 1998)).

Release of PYY [SEQ ID NO.: 2] occurs following a meal. An alternate molecular form of PYY is PYY[3-36] [SEQ ID NO.: 3] (Eberlein, Eysselein et al. *Peptides* 10: 797-803, 1989) (Grandt, Schimiczek et al. *Regul Pept* 51: 151-9, 1994). This fragment constitutes approximately 40% of total PYY-like immunoreactivity in human and canine intestinal extracts and about 36% of total plasma PYY immunoreactivity in a fasting state to slightly over 50% following a meal. It is apparently a dipeptidyl peptidase-IV (DPP4) cleavage product of PYY. PYY[3-36] is reportedly a selective ligand at the Y2 and Y5 receptors, which appear pharmacologically unique in preferring N-terminally truncated (i.e. C-terminal fragments of) NPY analogs. Peripheral administration of PYY reportedly reduces gastric acid secretion, gastric motility, exocrine pancreatic secretion (Yoshinaga, Mochizuki et al. *Am J Physiol* 263: G695-701, 1992) (Guan, Maouyo et al. *Endocrinology* 128: 911-6, 1991) (Pappas, Debas et al. *Gastroenterology* 91: 1386-9, 1986), gallbladder contraction and intestinal motility (Savage, Adrian et al. *Gut* 28: 166-70, 1987). The effects of central injection of PYY on gastric emptying, gastric motility and gastric acid secretion, as seen after direct injection in or around the hindbrain/brainstem (Chen and Rogers. *Am J Physiol* 269: R787-R792, 1995) (Chen, Rogers et al. *Regul Pept* 61: 95-98, 1996) (Yang and Tache. *Am J Physiol* 268: G943-8, 1995) (Chen, Stephens et al. *Neurogastroenterol Motil* 9: 109-116, 1997), may differ from those effects observed after peripheral injection. For example, centrally administered PYY had some effects opposite to those described herein for peripherally injected PYY [3-36] in that gastric acid secretion was stimulated, not inhibited. Gastric motility was suppressed only in conjunction with TRH stimulation, but not when administered alone, and was indeed stimulatory at higher doses through presumed interaction with PP receptors. PYY has been shown to stimulate food and water intake after central administration (Morley, Levine et al. *Brain Res* 341: 200-203, 1985) (Corp, Melville et al. *Am J Physiol* 259: R317-23, 1990).

Likewise, one of the earliest reported central effects of NPY [SEQ ID NO.: 4] was to increase food intake, particularly in the hypothalamus (Stanley, Daniel et al. *Peptides* 6: 1205-11, 1985). PYY and PP are reported to mimic these effects, and PYY is more potent or as potent as NPY (Morley, J. E., Levine, A. S., Grace, M., and Kneip, J. *Brain Res* 341: 200-203, 1985) (Kanatani, Mashiko et al. *Endocrinology* 141: 1011-6, 2000) (Nakajima, Inui et al. *J Pharmacol Exp Ther* 268: 1010-4, 1994). Several groups found the magnitude of NPY-induced feeding to be higher than that induced by any pharmacological agent previously tested, and also extremely long-lasting. NPY-induced stimulation of feeding has been reproduced in a number of species. Among the three basic macronutrients (fat, protein, and carbohydrate), the intake of carbohydrates was preferentially stimulated. No tolerance was seen towards the orexigenic effect of NPY, and when administration of the peptide was repeated over 10 days, a marked increase in the rate of weight gain was observed. Following starvation, the concentration of NPY in the hypothalamic PVN increased with time, and returned rapidly to control levels following food ingestion.

Pharmacological studies and cloning efforts have revealed a number of seven transmembrane receptors for the PP family of peptides, and these receptors have been assigned the names Y1 through Y6 (and a putative PYY-preferring receptor or Y7). Typical signaling responses of these receptors are similar to those of other $G_i/G_o$-coupled receptors, namely inhibition of adenylate cyclase. Even with fairly low sequence homology among receptors, it is apparent that there is a clustering of amino acid sequence similarity between Y1, Y4 and Y6 receptors, while Y2 and Y5 define other families. Other binding sites have been identified by the rank order of potency of various peptides. The NPY-preferring receptor, which has not been cloned, has been termed Y3, and PYY-preferring receptors have also been shown to exist (putative Y7) (Reviewed in (Michel, Beck-Sickinger et al. *Pharmacol Rev* 50:143-50, 1998) (Gehlert, D. R. *Proc Soc Exp Biol Med* 218: 7-22, 1998)).

The Y5 and Y1 receptors have been suggested as the primary mediators of the food intake response (Marsh, Hollopeter et al. *Nat Med* 4: 718-21, 1998) (Kanatani, A., Mashiko, S., Murai, N., Sugimoto, N., Ito, J., Fukuroda, T., Fukami, T., Morin, N., MacNeil, D. J., Van der Ploeg, L. H., Saga, Y., Nishimura, S., and Ihara, M. *Endocrinology* 141: 1011-6, 2000). The prevalent idea has been that endogenous NPY, via these receptors, increases feeding behavior. Proposed therapies for obesity have invariably been directed toward antagonism of NPY receptors, while therapies for treating anorexia have been directed toward agonists of this ligand family (see, e.g., U.S. Pat. Nos. 5,939,462; 6,013,622; and 4,891,357). In general, PYY and NPY are reported to be equipotent and equally effective in all Y1, Y5 (and Y2) receptor assays studied (Gehlert, D. R. *Proc Soc Exp Biol Med* 218: 7-22, 1998).

The main characteristic of putative Y3 receptors is that they recognize NPY, while PYY is at least an order of magnitude less potent. The Y3 receptor represents the only binding site/receptor that shows a preference for NPY.

There is an additional binding site/receptor which shows preference for PYYs, termed PYY-preferring receptor, which is referred to herein as the Y7 receptor (s). Different rank orders of binding to this receptor, or class of receptors, have been reported, suggesting that there may be more than one receptor in this family. In most cases it has been applied to describe a receptor where PYY was three to five times more potent than NPY. The International Union of Pharmacology recommendations for the nomenclature of NPY, PYY and PP receptors are that the term PYY-preferring receptor is not used unless a potency difference of at least twenty fold between PYY and NPY is observed (Michel, M. C., Beck-Sickinger, A., Cox, H., Doods, H. N., Herzog, H., Larhammar, D., Quirion, R., Schwartz, T., and Westfall, T. *Pharmacol Rev* 50: 143-50, 1998). However, for purposes of this disclosure, reference to the Y7 receptor or pharmacology of a PYY-preferring receptor means a receptor having any degree of preference for PYY over NPY.

Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. (see, e.g., (Kopelman. *Nature* 404: 635-43, 2000)). It reduces life-span and carries a serious risk of co-morbidities above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen, Heliovaara et al. *BMJ* 301: 835-7, 1990). Obesity is also a risk factor for the group of conditions called insulin resistance syndrome, or "Syndrome X." Recent estimates for the medical cost of obesity and associated disorders are $150 billion worldwide. The pathogenesis of obesity is believed to be multifactorial but the basic problem is that in obese subjects nutrient availability and energy expenditure do not come into balance until there is excess adipose tissue. Obesity is currently a poorly treatable, chronic, essentially intractable metabolic disorder. A therapeutic drug useful in weight reduction of obese persons could have a profound beneficial effect on their health.

All documents referred to herein are incorporated by reference into the present application as though fully set forth herein.

SUMMARY OF THE INVENTION

It has been discovered that, contrary to reported activities of central administration of members of the pancreatic polypeptide family, peripheral administration of PYY and PYY agonists reduces nutrient availability and is useful in the treatment of obesity and related disorders. PYY and PYY agonist compositions and uses thereof are disclosed herein to modulate nutrient availability in a patient for treating metabolic disorders which may be benefited by a reduction in nutrient availability. These methods will be useful in the treatment of, for example, obesity, diabetes, including but not limited to type 2 or non-insulin dependent diabetes, eating disorders, insulin-resistance syndrome, and cardiovascular disease.

By "PYY" is meant a Peptide YY polypeptide obtained or derived from any species. Thus, the term "PYY" includes both the human full length, 36 amino acid peptide as set forth in SEQ ID NO: 2, and species variations of PYY, including e.g., murine, hamster, chicken, bovine, rat, and dog PYY, for example. By "PYY agonist" is meant any compound which elicits an effect of PYY to reduce nutrient availability, for example a compound (1) having activity in the food intake, gastric emptying, pancreatic secretion, or weight loss assays described herein in Examples 1, 2, 5, or 6, and (2) which binds specifically in a Y receptor assay (Example 10) or in a competitive binding assay with labeled PYY or PYY[3-36] from certain tissues having an abundance of Y receptors, including e.g., area postrema (Example 9), wherein the PYY agonist is not pancreatic polypeptide. Preferably, PYY agonists would bind in such assays with an affinity of greater than 1 µM, and more preferably with an affinity of greater than 1-5 nM.

Such agonists can comprise a polypeptide having a functional PYY domain, an active fragment of PYY, or a chemical or small molecule. PYY agonists may be peptide or non-peptide compounds, and include "PYY agonist analogs," which refer to any compound structurally similar to a PYY that have PYY activity typically by virtue of binding to or otherwise directly or indirectly interacting with a PYY receptor or other receptor or receptors with which PYY itself may interact to elicit a biological response. Such compounds include derivatives of PYY, extended PYY molecules having more than 36 amino acids, truncated PYY molecules having less than 36 amino acids, and substituted PYY molecules having one or more different amino acids, or any combination of the above. Such compounds may also be modified by processes such as amidation, glycosylation, acylation, sulfation, phosphorylation, acetylation and cyclization.

One such PYY agonist analog is PYY[3-36], identified herein as SEQ ID NO: 3. Polypeptides with numbers in brackets refer to truncated polypeptides having the sequence of the full length peptide over the amino acid positions in the brackets. Thus, PYY[3-36] has a sequence identical to PYY over amino acids 3 to 36. A PYY agonist may bind to a PYY receptor with higher or lower affinity, demonstrate a longer or shorter half-life in vivo or in vitro, or be more or less effective than native PYY.

By "condition or disorder which can be alleviated by reducing caloric (or nutrient) availability" is meant any condition or disorder in a subject that is either caused by, complicated by, or aggravated by a relatively high nutrient availability, or that can be alleviated by reducing nutrient availability, for example by decreasing food intake. Such conditions or disorders include, but are not limited to, obesity, diabetes, including type 2 diabetes, eating disorders, and insulin-resistance syndromes.

In one aspect, the invention provides a method of treating obesity in an obese or overweight subject by administering a therapeutically effective amount of a PYY or a PYY agonist. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In other aspects, the invention features methods of reducing food intake, treating diabetes mellitus, and improving lipid profile (including reducing LDL cholesterol and triglyceride levels and/or changing HDL cholesterol levels) comprising administering to a subject a therapeutically effective amount of a PYY or a PYY agonist. In a preferred embodiment, the methods of the invention are used to treat conditions or disorders which can be alleviated by reducing nutrient availability in a subject in need thereof, comprising administering to said subject a therapeutically effective amount of a PYY or a PYY agonist. Such conditions and disorders include, but are not limited to, hypertension, dyslipidemia, cardiovascular disease, eating disorders, insulin-resistance, obesity, and diabetes mellitus of any kind.

In the methods of the invention, preferred PYY agonists are those having a potency in one of the assays described herein (preferably food intake, gastric emptying, pancreatic secretion, or weight reduction assays) which is greater than the potency of NPY in that same assay.

For all indications, in preferred embodiments, a preferred PYY agonist is PYY[3-36], and is preferably administered peripherally at a dose of about 1 µg to about 5 mg per day in single or divided doses, or at about 0.01 µg/kg to about 500 µg/kg per dose, more preferably about 0.05 µg/kg to about 250 µg/kg, most preferably below about 50 µg/kg. Dosages in these ranges will vary with the potency of each agonist, of course, and are readily determined by one of skill in the art.

In the methods of the present invention, PYY's and PYY agonists may be administered separately or together with one or more other compounds and compositions that exhibit a long term or short-term action to reduce nutrient availability, including, but not limited to other compounds and compositions that comprise an amylin or amylin agonist, a cholecystokinin (CCK) or CCK agonist, a leptin (OB protein) or leptin agonist, an exendin or exendin agonist, or a GLP-1 or GLP-1 agonist. Suitable amylin agonists include, for example, [25,28,29Pro-]-human amylin (also known as "pramlintide," and described in U.S. Pat. Nos. 5,686,511 and 5,998,367) and salmon calcitonin. The CCK used is preferably CCK octapeptide (CCK-8). Leptin is discussed in, for example, (Pelleymounter, Cullen et al. *Science* 269: 540-543, 1995) (Halaas, Gajiwala et al. *Science* 269: 543-6, 1995) and (Campfield, Smith et al. *Science* 269: 546-549, 1995). Suitable exendins include exendin-3 and exendin-4, and exendin agonist compounds include, for example, those described in PCT Publications WO 99/07404, WO 99/25727, and WO 99/25728.

DETAILED DESCRIPTION OF THE INVENTION

Figure 1:
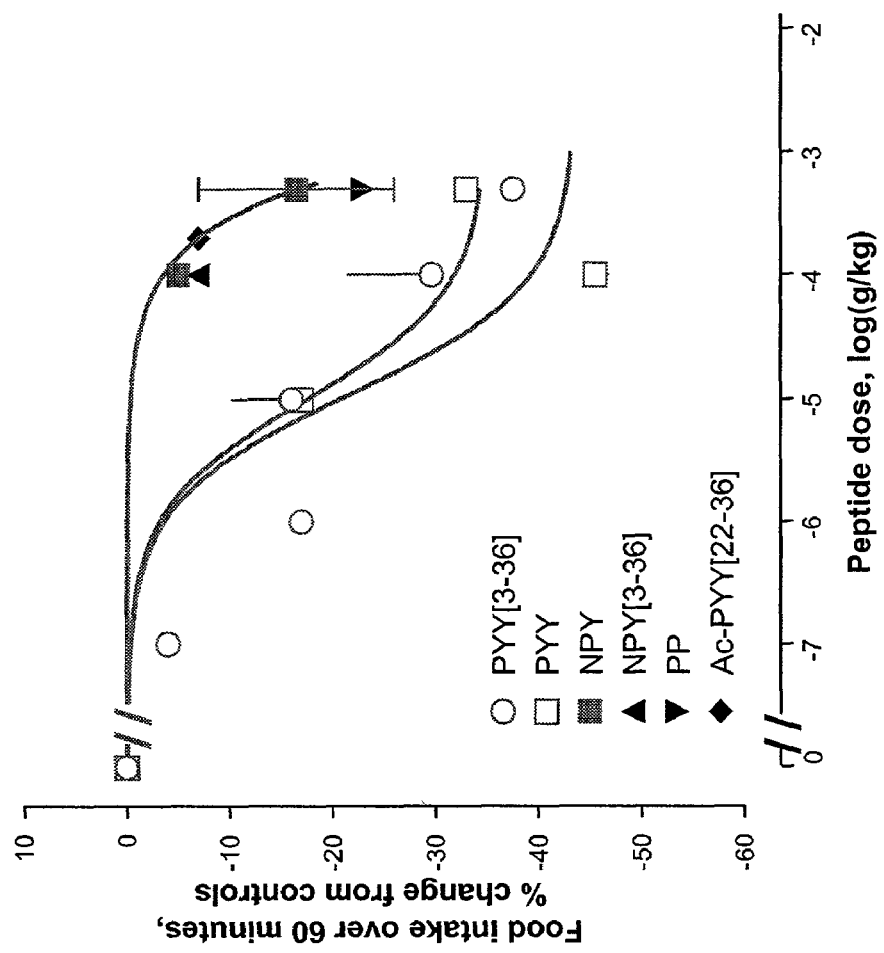
FIG. 1 is a plot of the activity of Y receptor ligands in a food intake assay in overnight-fasted NIH/SW mice.

It has been generally accepted that endogenous NPY (reviewed in (Schwartz, Woods, et al. *Nature* 404: 661-71, 2000)), and PYY (Morley, J. E., Levine, A. S., Grace, M., and Kneip, J. *Brain Res* 341: 200-203, 1985)), via their receptors, increase feeding behavior. Methods directed at therapies for obesity have invariably attempted to antagonize Y receptors, while claims for treating anorexia have been directed at agonists of this ligand family. However, as described and claimed herein, it has been surprisingly discovered that peripheral administration of PYY and agonists thereof has a potent effect to reduce nutrient availability, rather than increase it as suggested by reports in the patent and scientific literature (see e.g. U.S. Pat. Nos. 5,912,227 and 6,316,203 which disclose the use of PYY receptor agonists to increase weight gain). The spectrum of actions of inhibition of food intake, slowing of gastric emptying, inhibition of gastric acid secretion, and inhibition of pancreatic enzyme secretion, are useful to exert clinical benefit in metabolic diseases such as type 1, type 2, or gestational diabetes mellitus, obesity and other manifestations of insulin-resistance syndrome (Syndrome X), and in any other use for reducing nutrient availability.

Use of PYY and PYY agonists to reduce food intake and nutrient availability, and in treating disorders such as diabetes and obesity, has not been previously asserted. In fact, such utility in diabetes would not be predicted from the absence of acute effect on blood glucose and from reports of inhibition of insulin secretion. However, it is demonstrated herein that this group of ligands and agonist ligands will be useful in these condition and related conditions.

The Applicant's data demonstrate that the effects of peripherally-administered PYY or PYY[3-36] to reduce food intake and to delay gastric emptying are determined by interactions with one or more unique receptor classes in, or similar to, those in the Y-fold family. The data are best explained by interactions with a receptor or receptors similar to the PYY-preferring (or Y7) receptors, and are less well explained by interactions with the other known Y receptors such as Y1-Y6. Table 1 (below) shows published PP family ligand potencies reported at the known receptors, as well as certain unpublished data of Applicants, and the rank order of potencies of various ligands. The rank order of potency in the Examples herein does not correspond to any single published receptor pharmacology, and indicates a novel mechanism of PYY action in reducing caloric availability.

TABLE 1

Summary of receptor pharmacology for the PP family of receptors derived from published data and patents. The peripheral appetite and gastric emptying data are unpublished data of the Applicant.

| RECEPTORS | PHARMACOLOGY | REFERENCE |
|---|---|---|
| Food Intake Inhibition (peripheral) | PYY[3-36] ≧ PYY >> NPY = NPY[3-36] = PP = Ac-PYY[22-36] (See FIG. 1) | Applicant data |
| Gastric Emptying | PYY[3-36] ≧ PYY >> NPY = NPY[3-36] = PP = Ac-PYY[22-36] (See FIG. 2) | Applicant data |
| Food Intake Stimulation (central) | PYY ≧ PYY[3-36] = NPY = NPY[3-36] > PP | (Iyengar, Li et al. J Pharmacol Exp Ther 289: 1031-40, 1999) |

TABLE 1-continued

Summary of receptor pharmacology for the PP family of receptors derived from published data and patents. The peripheral appetite and gastric emptying data are unpublished data of the Applicant.

| RECEPTORS | PHARMACOLOGY | REFERENCE |
|---|---|---|
| Y1 | NPY = PYY > NPY[3-36] = PYY[3-36] = PP | (Iyengar, S., Li, D. L., and Simmons, R. M. J Pharmacol Exp Ther 289: 1031-40, 1999) (Gehlert, D. R. Proc Soc Exp Biol Med 218: 7-22, 1998; Michel, M. C., Beck-Sickinger, A., Cox, H., Doods, H. N., Herzog, H., Larhammar, D., Quirion, R., Schwartz, T., and Westfall, T. Pharmacol Rev 50: 143-50, 1998) U.S. Pat. No. 5,968,819 |
| Y2 | NPY = PYY = PYY[3-36] = NPY[3-36] >> PP | (Gehlert, D. R. Proc Soc Exp Biol Med 218: 7-22, 1998; Michel, M. C., Beck-Sickinger, A., Cox, H., Doods, H. N., Herzog, H., Larhammar, D., Quirion, R., Schwartz, T., and Westfall, T. Pharmacol Rev 50: 143-50, 1998; Iyengar, S., Li, D. L., and Simmons, R. M. J Pharmacol Exp Ther 289: 1031-40, 1999)US 5,968,819 |
| Y3 | NPY > PP > PYY | (Gehlert, D. R. Proc Soc Exp Biol Med 218: 7-22, 1998; Michel, M. C., Beck-Sickinger, A., Cox, H., Doods, H. N., Herzog, H., Larhammar, D., Quirion, R., Schwartz, T., and Westfall, T. Pharmacol Rev 50: 143-50, 1998) |
| Y4 | PP > PYY > NPY > PYY[3-36] = NPY[3-36] | (Gehlert, D. R. Proc Soc Exp Biol Med 218: 7-22, 1998; Michel, M. C., Beck-Sickinger, A., Cox, H., Doods, H. N., Herzog, H., Larhammar, D., Quirion, R., Schwartz, T., and Westfall, T. Pharmacol Rev 50: 143-50, 1998; Iyengar, S., Li, D. L., and Simmons, R. M. J Pharmacol Exp Ther 289: 1031-40, 1999) U.S. Pat. No. 5,968,819 |
| Y5 | NPY = PYY ≧ PP ≧ PYY[3-36] = NPY[3-36] | (Gehlert, D. R. Proc Soc Exp Biol Med 218: 7-22, 1998; Michel, M. C., Beck-Sickinger, A., Cox, H., Doods, H. N., Herzog, H., Larhammar, D., Quirion, R., Schwartz, T., and Westfall, T. Pharmacol Rev 50: 143-50, 1998; Iyengar, S., Li, D. L., and Simmons, R. M. J Pharmacol Exp Ther 289: 1031-40, 1999) U.S. Pat. No. 5,968,819 |
| Y6 | NPY = PYY ≧ NPY[3-36] > PP | (Gehlert, D. R. Proc Soc Exp Biol Med 218: 7-22, 1998; Michel, M. C., Beck-Sickinger, A., Cox, H., Doods, H. N., Herzog, H., Larhammar, D., Quirion, R., Schwartz, T., and Westfall, T. Pharmacol Rev 50: 143-50, 1998; Iyengar, S., Li, D. L., and Simmons, R. M. J Pharmacol Exp Ther 289: 1031-40, 1999) U.S. Pat. No. 5,968,819 |
| (Y7) | PYY > NPY >> PYY[3-36] = PP | (Yang, Li et al. Br J Pharmacol 123: 1549-54, 1998) |
| (Y7) | PYY[3-36] ≧ PYY > NPY >> PP | (Haynes, Hill et al. Br J Pharmacol 122: 1530-6, 1997) |
| (Y7) | PYY >> NPY = PYY[3-36] = PP | (Kawakubo, Yang et al. Brain Res 854: 30-4, 2000) |

Any PYY or PYY agonist may be useful in the invention. Preferred PYY agonists include peptide agonists, particularly PYY agonist analogs such as PYY[3-36]. Analogs may be made by, e.g., conservative amino acid substitution of the sequence of PYY or portions thereof, and can be tested in the assays provided in the Examples or other suitable assays that distinguish the actions of PYY from those of NPY or PP. Non-peptide agonists are also contemplated.

The spectrum of actions exhibited by PYY, e.g., inhibition of food intake, slowing of gastric emptying, inhibition of gastric acid secretion, inhibition of pancreatic enzyme secretion, etc., act in a coordinated way to restrict nutrient assimilation and thereby exert clinical benefit in metabolic diseases such diabetes mellitus, obesity, cardiovascular disease (atherosclerosis, hypertension, dyslipidemia, etc.), and manifestations of insulin-resistance syndromes (e.g., Syndrome X).

The human sequences of peptides in the PP ligand family referred to herein are as follows (in conventional one-letter amino acid code):

```
PP:        APLEPVYPGDNATPEQMAQYAADLRRYINMLTRPRY (SEQ ID NO: 1)

PYY:       YPIKPEAPGEDASPEELNRYYASLRHYLNLVTRQRY (SEQ ID NO: 2)

PYY[3-36]: IKPEAPGEDASPEELNRYYASLRHYLNLVTRQRY   (SEQ ID NO: 3)

NPY:       YPSKPDNPGEDAPAEDMARYYSALRHYINLITRQRY (SEQ ID NO: 4)
```

These peptides are C-terminally amidated when expressed physiologically, but need not be for the purposes of the instant invention. These peptides may also have other post-translational modifications.

PYY and peptide-based PYY agonists described herein may be prepared using standard recombinant expression or chemical peptide synthesis techniques known in the art, e.g., using an automated or semiautomated peptide synthesizer.

Solid phase peptide synthesis may be carried out with an automatic peptide synthesizer (e.g., Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Peptides may be also be assembled using an Advanced Chem Tech Synthesizer (Model MPS 350, Louisville, Ky.). Peptides may be purified by RP-HPLC (preparative and analytical) using, e.g., a Waters Delta Prep 3000 system and a C4, C8 or C18 preparative column (10µ, 2.2×25 cm; Vydac, Hesperia, Calif.).

Peptide compounds useful in the invention may also be prepared using recombinant DNA techniques, using methods now known in the art. See, e.g., Sambrook et al., Molecular Cloning: A Laboratory Manual, 2d Ed., Cold Spring Harbor (1989). Non-peptide compounds useful in the present invention may be prepared by art-known methods. For example, phosphate-containing amino acids and peptides containing such amino acids, may be prepared using methods known in the art. See, e.g., Bartlett and Landen, *Biorg. Chem.* 14:356-377 (1986).

The compounds described above are useful in view of their pharmacological properties. In particular, the compounds of the invention possess activity as agents to reduce nutrient availability, including reduction of food intake.

The compositions or pharmaceutical composition can be administered by any route, including intravenously, intraperitoneal, subcutaneous, and intramuscular, orally, topically, transmucosally, or by pulmonary inhalation. Compositions useful in the invention may conveniently be provided in the form of formulations suitable for parenteral (including intravenous, intramuscular and subcutaneous), nasal or oral administration. In some cases, it will be convenient to provide a PYY or a PYY agonist and another food-intake-reducing, plasma glucose-lowering or plasma lipid-altering agent, such as an amylin, an amylin agonist, a CCK or CCK agonist, or a leptin or leptin agonist, or an exendin or exendin agonist, in a single composition or solution for administration together. In other cases, it may be more advantageous to administer the additional agent separately from said PYY or PYY agonist.

A suitable administration format may best be determined by a medical practitioner for each patient individually. Various pharmaceutically acceptable carriers and their formulation are described in standard formulation treatises, e.g., Remington's Pharmaceutical Sciences by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for e.g., injection or infusion. Preferably, they are suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

Since the products of the invention are amphoteric, they may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available. Such products are readily prepared by procedures well known to those skilled in the art.

For use by the physician, the compositions will be provided in dosage unit form containing an amount of a PYY or a PYY agonist with or without another active ingredient, e.g., a food intake-reducing, plasma glucose-lowering or plasma lipid-altering agent. Therapeutically effective amounts of a PYY or a PYY agonist for use in reducing nutrient availability are those that suppress appetite at a desired level. As will be recognized by those in the field, an effective amount of therapeutic agent will vary with many factors including the age and weight of the patient, the patient's physical condition, the blood sugar level, the weight level to be obtained, and other factors The effective daily appetite-suppressing dose of the compounds will typically be in the range of about 1 to 30 µg to about 5 mg/day, preferably about 10 to 30 µg to about 2 mg/day and more preferably about 5 to 100 µg to about 1 mg/day, most preferably about 5 µg to about 500 µg/day, for a 50 kg patient, administered in a single or divided doses. Preferably, dosages are between about 0.01 to about 100 µg/kg/dose. The exact dose to be administered is readily determined by one of skill in the art and is dependent upon the potency of the particular compound, as well as upon the age, weight and condition of the individual. Administration should begin whenever the suppression of nutrient availability, food intake, weight, blood glucose or plasma lipid lowering is desired, for example, at the first sign of symptoms or shortly after diagnosis of obesity, diabetes mellitus, or insulin-resistance syndrome. Administration may be by any route, e.g., injection, preferably subcutaneous or intramuscular, oral, nasal, transdermal, etc. Dosages for certain routes, for example oral administration, should be increased to account for decreased bioavailability, for example, by about 5-100 fold.

The optimal formulation and mode of administration of compounds of the present application to a patient depend on factors known in the art such as the particular disease or disorder, the desired effect, and the type of patient. While the compounds will typically be used to treat human subjects they may also be used to treat similar or identical diseases in other vertebrates such as other primates, farm animals such as swine, cattle and poultry, and sports animals and pets such as horses, dogs and cats.

Screening for Additional PYY Agonists

Other PYY agonists can be identified by using the receptor binding assays described below (e.g., in Examples 9 and 10) or known in the art in combination with the physiological screens described in the Examples below. Potential PYY agonists can be compared with the activity of PYY or PYY [3-36].

Alternatively, once one or more PYY-preferring (Y7) receptors have been characterized and cloned, alternative assays and high throughput screens can be implemented as discussed below or known in the art. Y7 receptors are those with an affinity for PYY or PYY[3-36] greater than their affinity for NPY. Methods of screening for compounds which modulate PYY receptor activity comprise contacting test compounds with PYY receptors and assaying for the presence of a complex between the compound and the PYY receptors. In such assays, the test ligand is typically labelled. After suitable incubation, free ligand is separated from that present in bound form, and the amount of free or uncomplexed label is a measure of the ability of the particular compound to bind to the PYY receptors. Alternatively, bound labelled ligand may be measured (e.g., using expressed membrane-bound Y7 receptors).

In another embodiment of the invention, high throughput screening for compounds having suitable binding affinity to PYY receptors is employed. For example, large numbers of different small peptide test compounds are synthesised on a solid substrate. The peptide test compounds are contacted with the PYY receptor and washed. Bound PYY receptor is then detected by methods well known in the art. Purified test compounds can also be coated directly onto plates for use in the aforementioned drug screening techniques. In addition, if the test compounds are proteins, antibodies can be used to capture the protein and immobilize it on the solid support by any means known in the art.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with a PYY agonist. Radiolabeled competitive binding studies are described in A. H. Lin et al. *Antimicrobial Agents and Chemotherapy*, 1997, vol. 41, no. 10. pp. 2127-2131, the disclosure of which is incorporated herein by reference in its entirety.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

In experiments described below, members of the PP ligand family were used in various assays. Unless otherwise stated, all peptide test compounds were dissolved in saline to a concentration of between 1-5 mg/ml without measurement of pH. In all cases, preparations were clear to the eye prior to administration.

Example 1

Activity of Y Receptor Ligands on Food Intake in Overnight-Fasted NIH/SW Mice

Female NIH/Swiss mice (8-12 weeks old) were group housed with a 12:12 hour light:dark cycle with lights on at 0600. Water and a standard pelleted mouse chow diet were available ad libitum, except as noted. Animals were fasted and housed individually starting at approximately 1500 hrs, 1 day prior to experiment. The morning of the experiment (approx. 0630 hrs), all animals were weighed and divided into experimental groups so as to give the most similar weight distribution between groups. In a typical study, n=10 for the control group and at least 5 for each treatment group.

At time=0 min, all animals were given an intraperitoneal injection of vehicle or compound in a volume of 5 ml/kg and immediately given a pre-weighed amount (10-15 g) of the standard chow. Increasing dosages of PYY[3-36], or PYY (0.1 µg/kg to 500 µg/kg and NPY (100 and 500 µg/kg), and single high doses of NPY[3-36] (100 µg/kg), N-terminal acetylated Ac-PYY[22-36] (200 µg/kg) and PP (500 µg/kg) were provided, as indicated on FIG. 1. Food was removed and weighed at 1 hr to determine the amount of food consumed (Morley, Flood et al. *Am J Physiol* 267: R178-R184, 1994).

Analysis:

Food intake was calculated by subtracting the weight of the food remaining after one hour from the weight of the food provided initially at time=0. The effects of treatment on food intake are expressed as % change relative to control.

Significant treatment effects were identified by ANOVA ($p<0.05$). Where a significant difference existed, test means were compared to the control mean using Dunnett's test (Prism v2.01, GraphPad Software Inc., San Diego, Calif.).

Results:

As seen in FIG. 1, PYY administered peripherally (intraperitoneal injection) at doses of 10, 100 and 500 µg/kg significantly reduced food intake measured over 60 min in overnight-fasted female NIH/SW mice. These doses of PYY[3-36] had approximately equal efficacy. PP and NPY showed a trend toward activity at 500 µg/kg. But NPY and NPY[3-36] [SEQ ID NO.: 5] were inactive at 100 µg/kg. Ac-PYY[22-36] [SEQ ID NO.: 6] at 200 µg/Kg and was also inactive. The rank order of potency was: PYY[3-36]≧PYY>>NPY=NPY[3-

36]=PP=Ac-PYY[22-36]. The rank order of potency, and in particular the lack of effect of NPY, does not reflect the pharmacology of any of the known cloned receptors.

PP given peripherally has been reported to reduce feeding (Asakawa, Inui et al. *Peptides* 20: 1445-8, 1999). Additionally, PP given peripherally to obese mice reportedly reduced food intake and body weight gain (Malaisse-Lagae, Carpentier et al. *Experientia* 33: 915-7, 1977). The ob/ob mouse is reported to be hypersensitive to several anorexigens (Young and Bhavsar. *Program and Abstracts, 10th International Congress of Endocrinology* 419 (poster P2-58), 1996). Mice over expressing PP were reported to decrease body weight and food intake (Ueno, Inui et al. *Gastroenterology* 117: 1427-32, 1999). Applicants were unable to reduce food intake with PP in the test system indicated in FIG. 1. The Asakawa et al. studies were acute single-injection studies and no data on body weight change were provided. Although the PP transgenic mouse study (Ueno et al., *Gastroenterology* 117: 1427-32, 1999) claims to show decreased body weight and food intake in overexpressing animals, half of the animals died in the perinatal period, which could signal pathophysiology apart from a straightforward explanation of decreased milk intake leading to starvation. In addition, the gene expression system is not pancreas-specific, and peptide is expressed in the brain, which confuses any interpretation of the over-expression data. Ueno et al. conclude from their data that PP could be involved in feeding and body weight regulation partly through regulation of GE, but the data in Examples 1 and 2 (below) show PP to have little or no effect on food consumption, and to be essentially inactive in slowing gastric emptying. Importantly, PP is only 50% homologous to PYY (or NPY), has a different primary tissue localization (pancreas vs. intestinal L-cells vs. neurons), and an apparent preference for the Y4 receptor over Y1 and Y2. NPY, which is 70% homologous to PYY, is a powerful orexigen when administered centrally. It produces only a modest decrease in food intake, and is completely inactive in the gastric emptying assay of Example 2 (below) when given peripherally.

Example 2

Activity of Y Peptide Ligands on Gastric Emptying in HSD Rats

Male HSD rats, 180-215 g, were housed with a 12:12 hour light:dark cycle and fasted for 20 hrs (overnight). At time=0 min, test peptide (PYY[3-36], PYY, Ac-PYY[22-36], NPY, NPY[3-36], or PP) or saline vehicle was injected (intraperitoneal) into conscious rats (n=6/group). At t=1 min, a solution of 1 mL sterile water containing 5 µCi of $^3$H-3-O-methyl-glucose was gavaged by oropharyngeal tube to conscious rats. Blood samples (10 µl) were collected 40 min after gavage and assayed for counts per minute (CPM) in plasma. To eliminate pain during tail vein sampling, 2% Lidocaine (0.1 ml) was injected 3-4 cm from the end of the tail (Gedulin, Jodka et al. *Gastroenterology* 108: A604, 1995).

Data Analysis:

Effects of the test compound were expressed as percent change relative to control, which was calculated as −100*(1− (mean value test rats/mean value controls)).

Relative activity was defined as significant if p<0.05 as determined by ANOVA. Where a significant difference existed, test means were compared to the control mean using Dunnett's test (Prism v2.01, GraphPad Software Inc., San Diego, Calif.).

Figure 2:
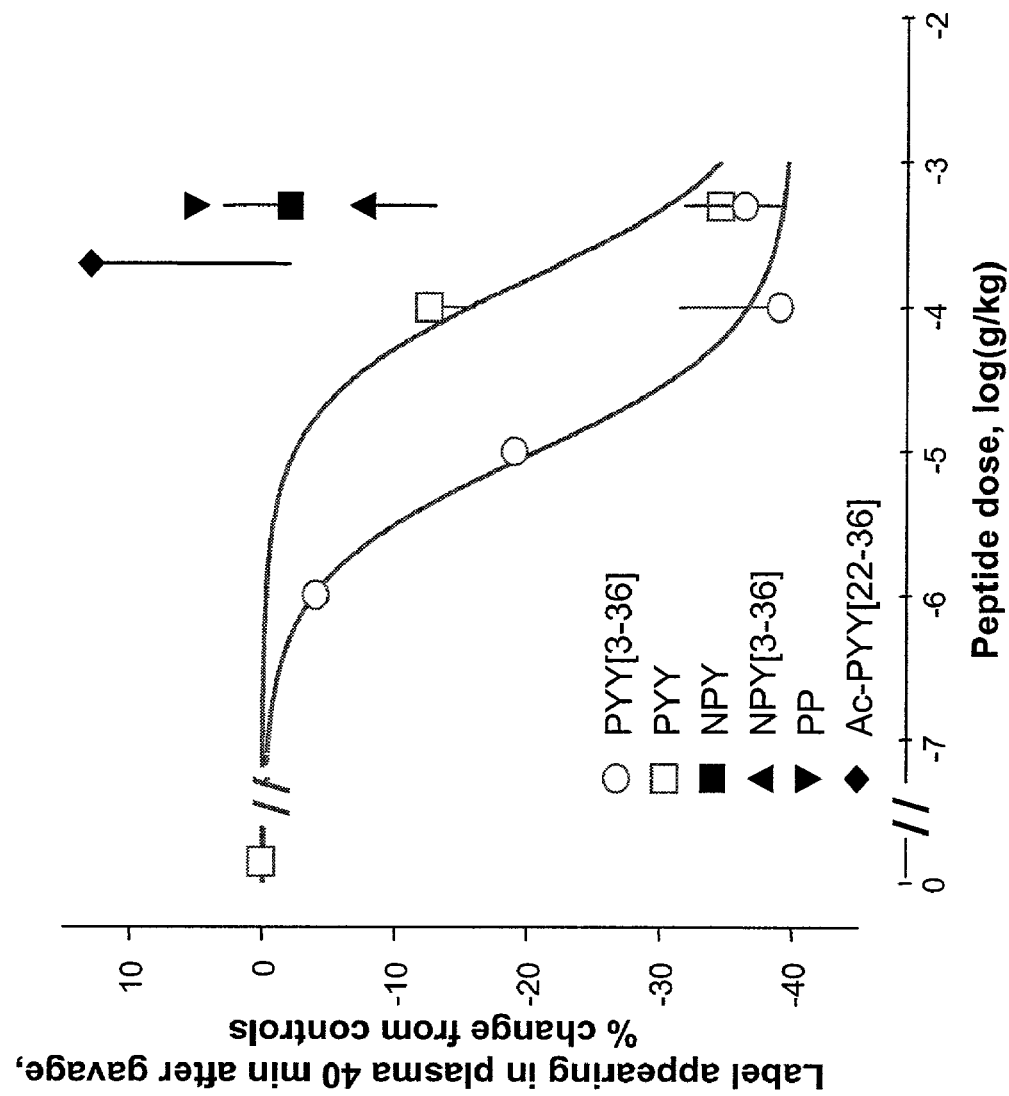
FIG. 2 is a plot of activity of various Y receptor ligands on gastric emptying in HSD rats.

Results:

As seen in FIG. 2, PYY[3-36] administered peripherally (intraperitoneal injection) at doses greater or equal to 10 µg/kg significantly and dose-dependently reduced gastric emptying measured at 40 minutes in HSD rats. PYY at 100 and 500 µg/kg was also efficacious. By contrast, NPY, NPY [3-36], or PP injected at 500 µg/kg and Ac-PYY[22-36] at 200 µg/kg were inactive. The order of potency of the test compounds is as follows: PYY[3-36]≧PYY>>NPY= NPY[3-36]=PP=Ac-PYY[22-36]. This potency profile is similar to that seen for food intake (FIG. 1). The lack of effect of NPY does not reflect the pharmacology of any known cloned receptors. It is significant that Ac-PYY[22-36] was inactive in both assays, since Balasubramanian et al., U.S. Pat. No. 5,604,203 reported that this subpeptide is a ligand for both rat intestinal PYY receptors, and the Y2 receptor.

Example 3

Acute Peripheral Administration of PYY[3-36] Inhibits Gastric Acid Secretion in Rats Male Harlan Sprague Dawley rats were housed in a 12:12 hour light:dark cycle. All experiments were performed during the light cycle. Animals were fasted for approximately 20 hours before experimentation but were given free access to water until the start of the experiment.

Rats (age 11-16 weeks, body mass 291-365 g) were surgically fitted with gastric fistulae (Kato, Martinez et al. *Peptides* 16: 1257-1262, 1995). Overnight fasted rats were weighed and their gastric fistulae were uncapped and attached to flexible Tygon tubing (⅜×1/16) into which was fitted a piece of PE205 tubing that would extend up into the stomach. Saline was injected through the narrower PE205 tubing and the effluent collected from the Tygon tubing. To ensure proper flow through the fistulae and an empty stomach, the stomach was flushed several times with ~5 mL of room temperature saline solution until flow was easy and the effluent was clean. Gastric acid secretion was measured at 10 min intervals by injecting 5 mL of saline followed by 3 mL of air and collecting the effluent. Three mL of each gastric aspirate were titrated to pH 7.0 with 0.01 N sodium hydroxide using a pH meter. The amount of base required for each titration, corrected to the total volume collected, was used to calculate the moles of acid in each sample.

After a baseline sample was collected, and the recovered volume recorded, the animal was given a subcutaneous injection of 125 µg/kg pentagastrin to stimulate gastric secretion. Gastric acid secretion was sampled every 10 minutes. Forty minutes after pentagastrin injection, the animal was given a subcutaneous injection of 100 µg/kg PYY[3-36] or saline and sampling of gastric secretion was continued every 10 minutes for a total of 2 hrs. Data are expressed as µmol of acid secreted per 10 minute sampling interval (mean±SEM n=4/group).

Figure 3:
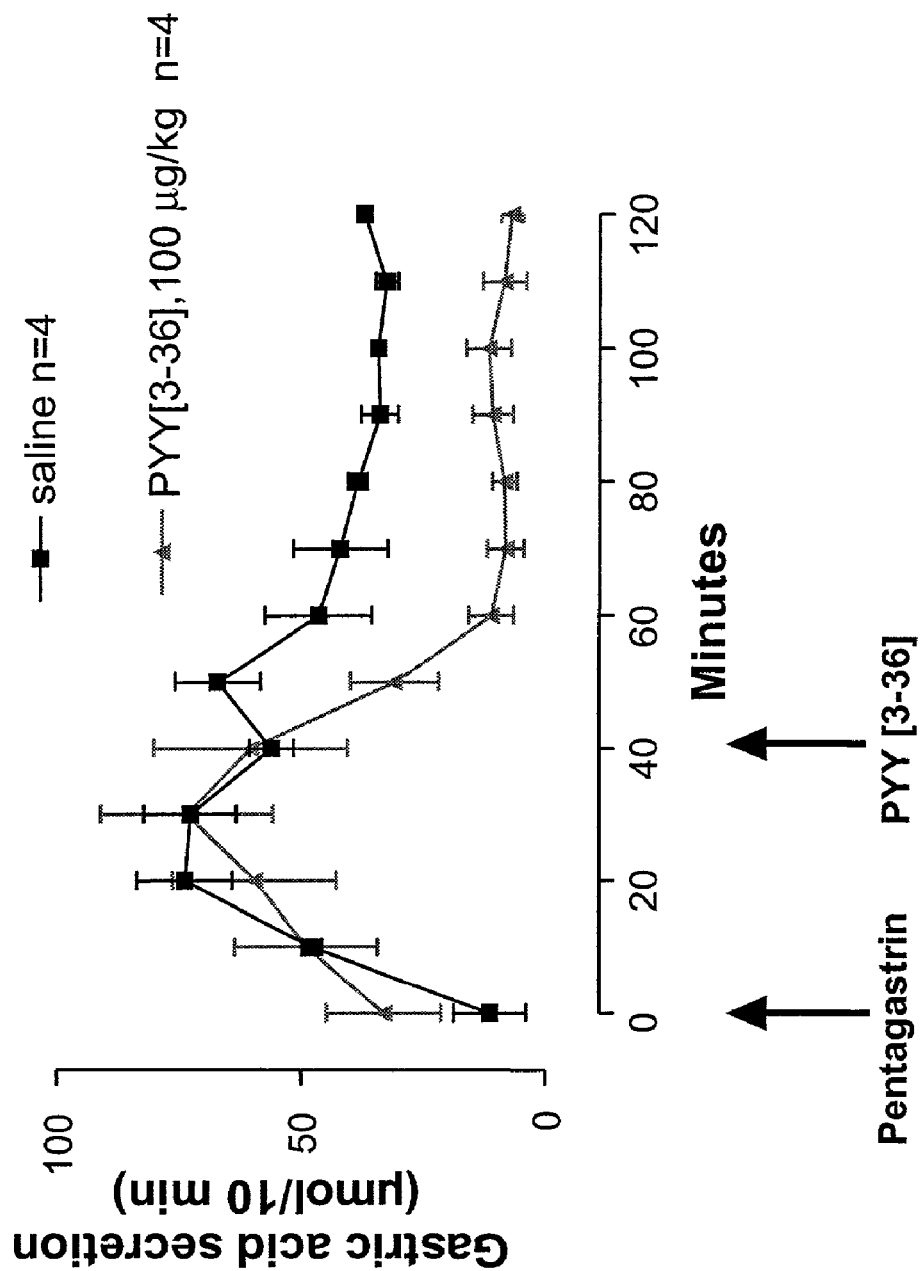
FIG. 3 demonstrates inhibition of gastric acid secretion in rats upon acute peripheral administration of PYY[3-36]. Data are expressed as µmol of acid secreted/10 min.

Results:

FIG. 3 demonstrates that PYY[3-36] administered acutely by peripheral (intraperitoneal) injection (100 µg/kg) inhibited pentagastrin-stimulated gastric acid secretion in rats. The $ED_{50}$ for this effect was ≈20 µg/kg.

Example 4

Acute Peripheral Administration of PYY[3-36] Prevents Gallbladder Emptying in Mice—Reversible by CCK-8

Figure 4:
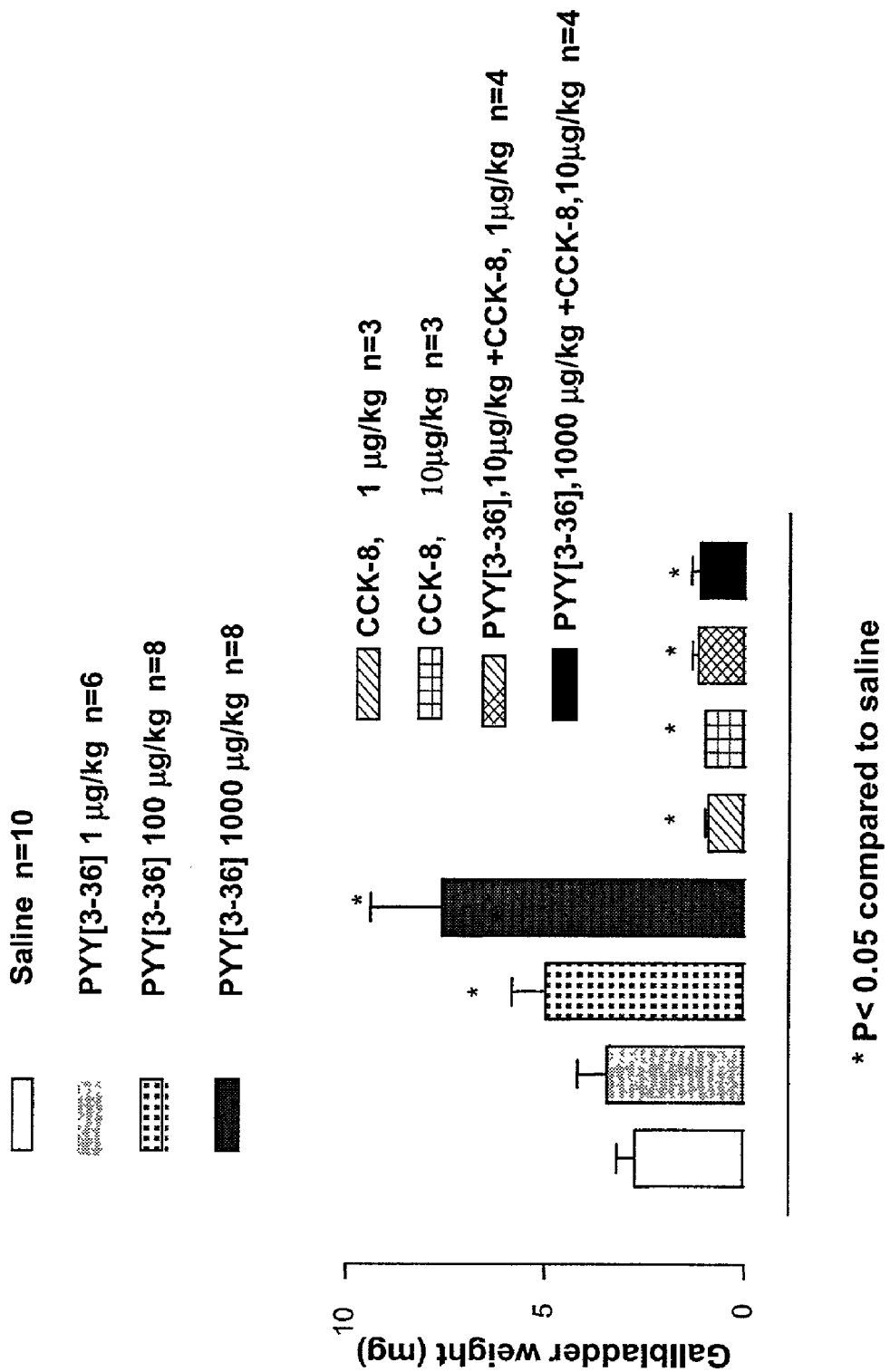
FIG. 4 is a bar graph demonstrating that acute peripheral administration of PYY[3-36] prevents gallbladder emptying in mice. This effect could be reversed by administration of CCK-8.

Mice were housed in a 12:12 hour light:dark cycle room with free access to water and mouse chow until the start of the experiment. At t=0, mice were given a subcutaneous injection of 1, 10, 100, or 1000 μg/kg PYY[3-36], 1 or 10 μg/kg CCK-8, both or saline (treatment and n/group as indicated in FIG. 4). Thirty minutes later, animals were anesthetized, and their intact gallbladders removed and weighed.

Analysis:

Data are expressed as organ weight in mg. Activity was defined as change from the mean of the control group. Statistical significance was defined as p<0.05 by ANOVA and/or Dunnett's test.

Results:

As seen in FIG. 4, PYY[3-36] administered by acute peripheral injection at doses greater or equal to 10 μg/kg prevented gallbladder emptying in mice. This inhibition of emptying had an $ED_{50} \approx 31$ μg/kg and could be overridden by CCK-8, even at the highest doses of PYY[3-36] tested.

Example 5

Acute Peripheral Administration of PYY[3-36] Inhibits CCK-8-Stimulated Exocrine Pancreatic Secretion (Amylase) in Rats Male Harlan Sprague Dawley rats were housed in a 12:12 hour light:dark cycle. All experiments were performed during the light cycle. Animals were fasted for approximately 20 hours before experimentation but were given free access to water until the start of the experiment.

Rats were anesthetized with 5% halothane, maintained with 2% halothane during surgery and with 1% halothane thereafter. Tracheotomy and cannulation of the right femoral artery were performed and body temperature was controlled with a thermoregulator that switched a heated operating table. The femoral arterial line, used for blood sampling, was perfused with heparinized saline (2 U/ml) and connected to a pressure transducer for blood pressure recording. Through a midline incision, two polyethylene cannulae were inserted into the common bile-pancreatic duct at a point about 0.5 cm above where the duct enters the pancreas. The first cannula was inserted up toward the liver to collect bile. The other end of this cannula was placed into the duodenum through a small incision in the duodenum. Thus, bile flowed directly from the liver to the small intestine, being shunted away from the pancreas completely. A second polyethylene cannula inserted into the common bile-pancreatic duct near the first was directed toward the pancreas to collect pancreatic juice. The pancreatic duct was ligated at its entry into the duodenum, forcing secreted pancreatic juice into the collection cannula.

Pancreatic juice was collected over 15 min intervals between t=−15 to +60 min. The volume of pancreatic juice (measured by weight) and activities of amylase were determined for each 15-minute aliquot (Taniguchi, Yazaki et al. *Eur J Pharmacol* 312: 227-33, 1996). Pancreatic juice was diluted 1:2000 before assay. Enzyme secretion was expressed in units per 15 min obtained by multiplying activity by volume collected (Taniguchi, H., Yazaki, N., Yomota, E., Shikano, T., Endo, T., and Nagasaki, M. *Eur J Pharmacol* 312: 227-33, 1996).

Statistical Analysis.

Pairwise statistical analyses were performed using Student's t-test; multiple comparisons to a control used Dunnett's test; general effects were tested by one-way ANOVA. Results are reported as mean± standard error of the mean. P<0.05 is used as the level of significance.

Figure 5:
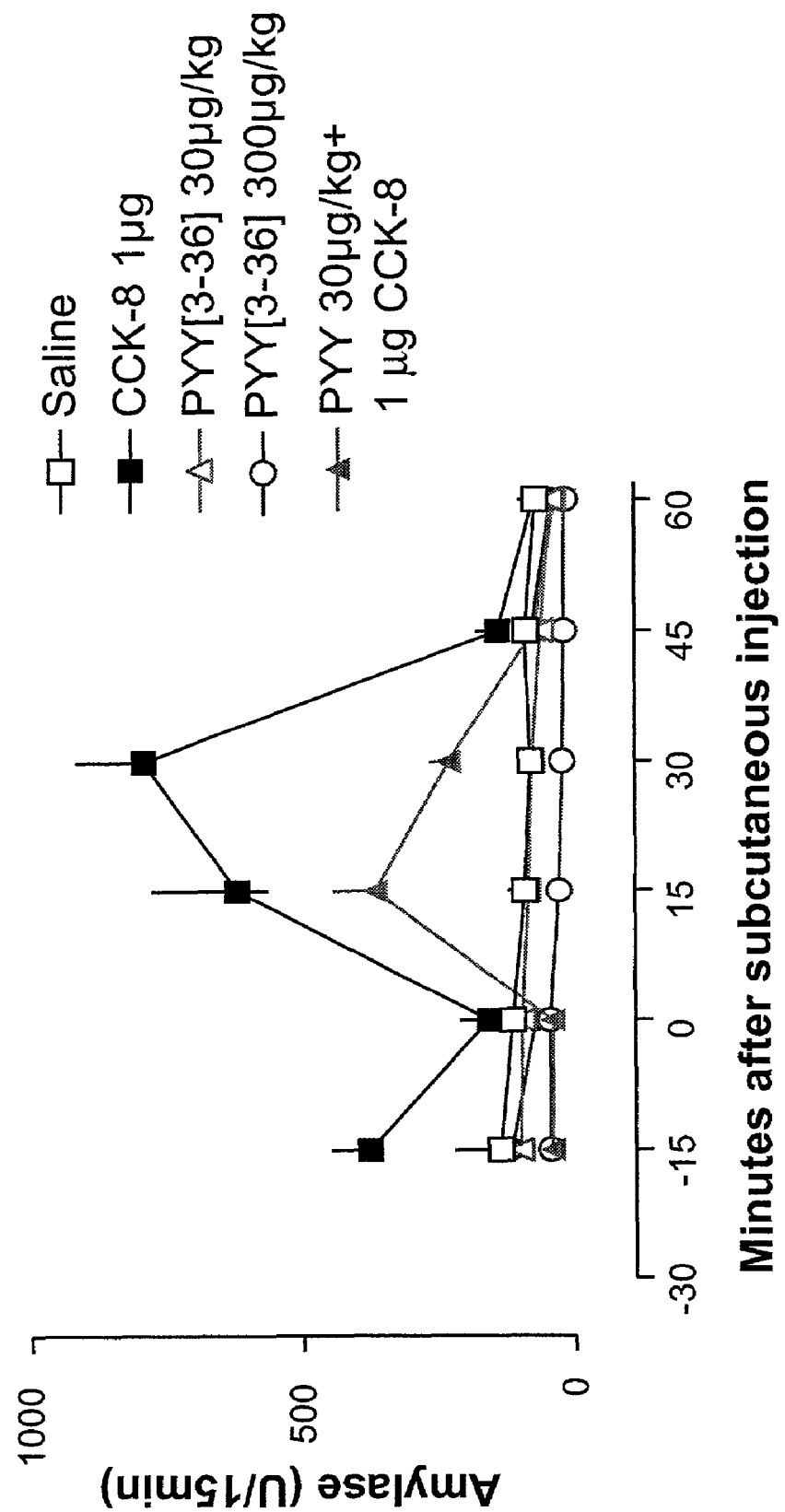
FIG. 5 shows an acute, dose-dependent effect of subcutaneously administered PYY[3-36] to inhibit CCK-8-stimulated exocrine pancreatic secretion (assayed by amylase activity) in rats.

Results:

FIG. 5 shows that PYY[3-36] administered by acute peripheral (subcutaneous) injection at 30 μg/kg blocked CCK-8-stimulated pancreatic secretion in rats as measured by amylase activity in pancreatic juice. In the absence of CCK-8, PYY[3-36] at 300 μg/kg had no effect on basal amylase activity when compared to saline-injected controls.

Example 6

Continuous Peripheral PYY[3-36] Infusion Decreases Body Weight Gain in Fattened C57Bl/6 (DIO) Mice Male C57Bl/6 mice (4 weeks-old at start of study) were fed high fat (HF; 58% of dietary kcal as fat) or low fat (LF; 11% of dietary kcal as fat) chow. After 7 weeks on chow, each mouse was implanted with an osmotic pump (Alzet #2004) that delivered the dose indicated in FIG. 6 of PYY[3-36] (30, 100, 300, or 1000 μg/kg/day) continuously for 4 weeks. Body weight and food intake were measured weekly (Surwit, Feinglos et al. *Metabolism—Clinical and Experimental* 44: 645-651, 1995).

Data Analysis:

Effects of the test compound are expressed as the mean±sd of change in grams from starting weight of at least 14 mice per treatment group ((p<0.05 ANOVA, Dunnett's test (Prism v2.01, GraphPad Software Inc., San Diego, Calif.).

Figure 6:
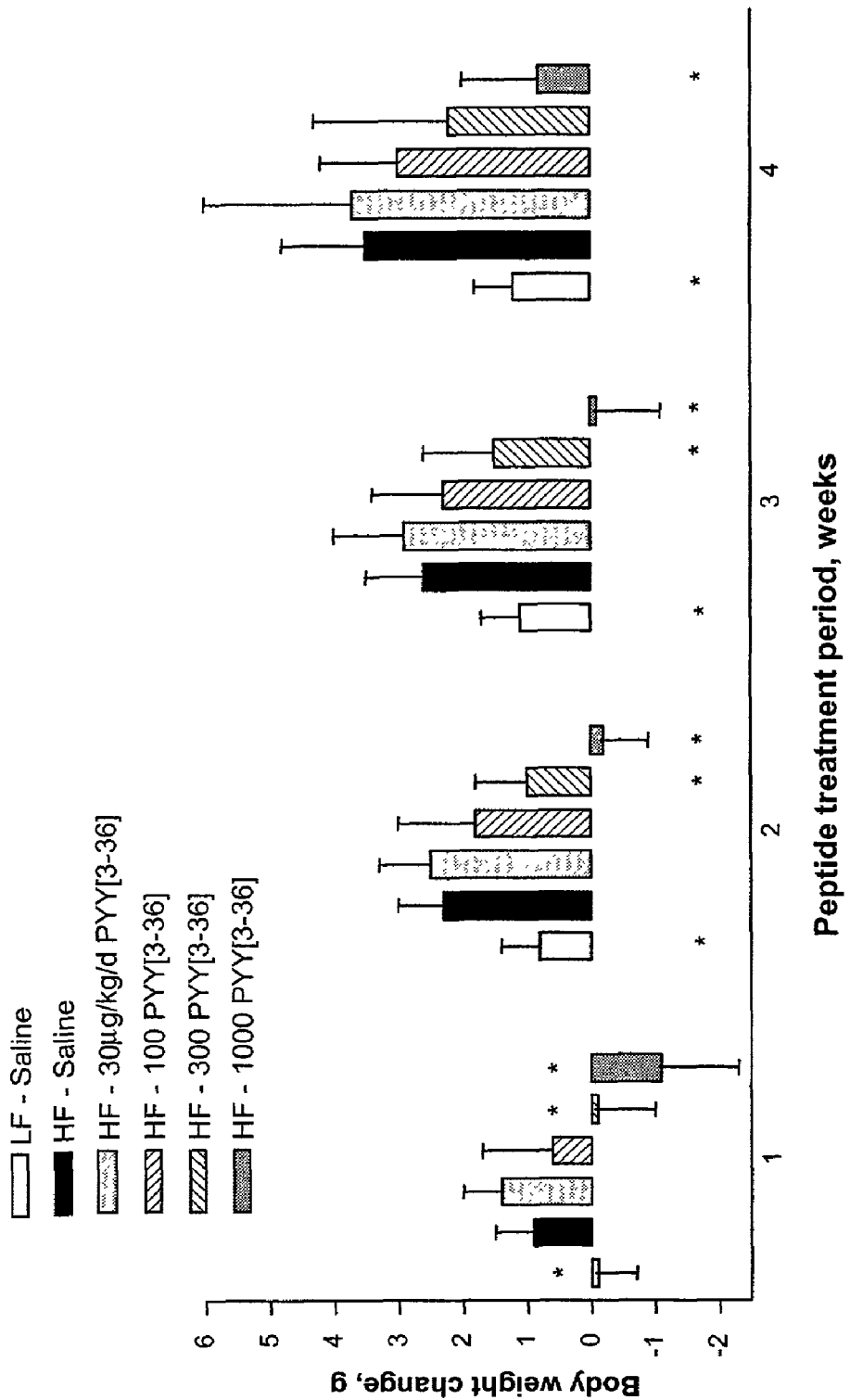
FIG. 6 illustrates a decreased body weight gain in fattened C57BI/6 (diet-induced obese, or DIO) mice with continuous peripheral PYY[3-36] infusion over a period of four weeks.

Results:

FIG. 6 demonstrates that PYY[3-36] administered by continuous peripheral infusion produced a dose-related decrease in body weight gain in diet-induced obese (DIO) mice. The effects were significant at 300 μg/kg/day for the first 3 weeks and at all time points for the 1000 μg/kg/day dose.

Example 7

Continuous Peripheral Infusion of PYY[3-36] Decreases Caloric Efficiency in Fattened C57Bl/6 (DIO) Mice Male C57Bl/6 mice (4 weeks-old at start of study) were fed high fat (HF; 58% of dietary kcal as fat) or low fat (LF; 11% of dietary kcal as fat) chow. After 7 weeks on chow, each mouse was implanted with an osmotic pump (Alzet #2004) that delivered the dose indicated in FIG. 6 of PYY[3-36] (30, 100, 300, or 1000 μg/kg/day) continuously for 4 weeks. Body weight and food intake were measured weekly (Surwit, Feinglos, et al *Metabolism—Clinical and Experimental* 44: 645-651, 1995).

Analysis:

Effects of the test compound are expressed as change in body weight (g) from the starting weight per kcal consumed. Kcal consumed was computed by multiplying the weight of food consumed (g) by the caloric density (kcal/g) specified by the manufacturer. Note that these data are derived from the animals used in Example 3.

Activity was defined as the change of the mean±sd of n=at least 14 mice/group. Significance was defined as p<0.05 in an ANOVA or Dunnett's test.

Figure 7:
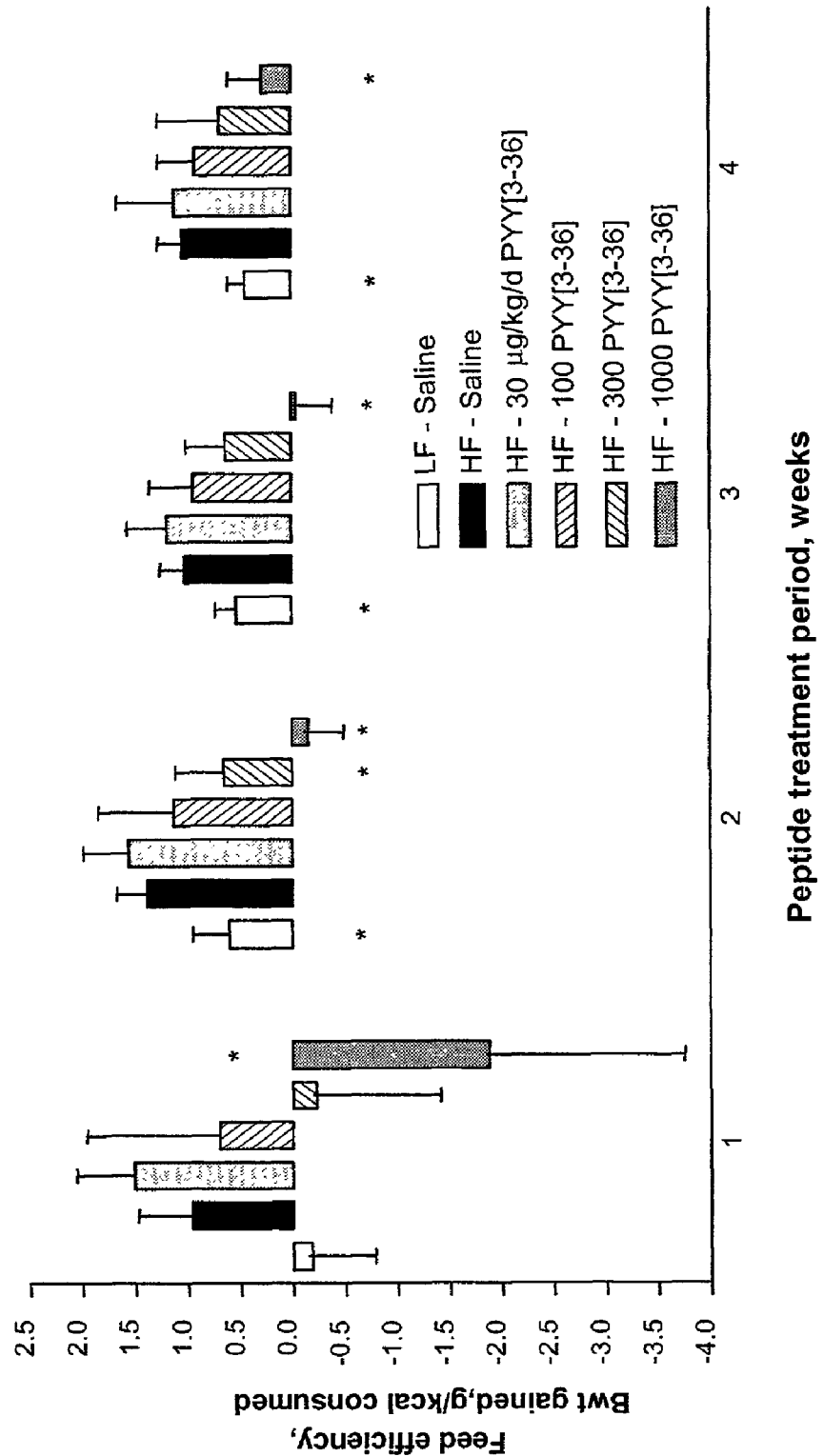
FIG. 7 shows the effect of continuous peripheral infusion of PYY[3-36] to decrease caloric efficiency in fattened C57BI/6 (diet-induced obese, or DIO) mice over a period of four weeks.

Results:

FIG. 7 shows that PYY[3-36] administered subchronically by continuous peripheral infusion produced a dose-related decrease in caloric efficiency (measured as body weight gained/kcal consumed) in diet-induced obese (DIO) mice.

The effects were significant at all time points for 1000 μg/kg/day and at some time points for 300 μg/kg/day.

Example 8

Continuous Peripheral Infusion of PYY[3-36] for 28-Days Improves Glycemic Control in Obese Diabetic (ZDF) Rats Diabetic fatty Zucker rats (ZDF) (7 weeks of age) were housed in a 12:12 hour light:dark cycle room and given ad libitum access to high fat rodent chow and water. After 1 week of acclimatization, blood samples were drawn, and animals were sorted by starting HbA1c to provide a similar range in each treatment group.

Figure 8:
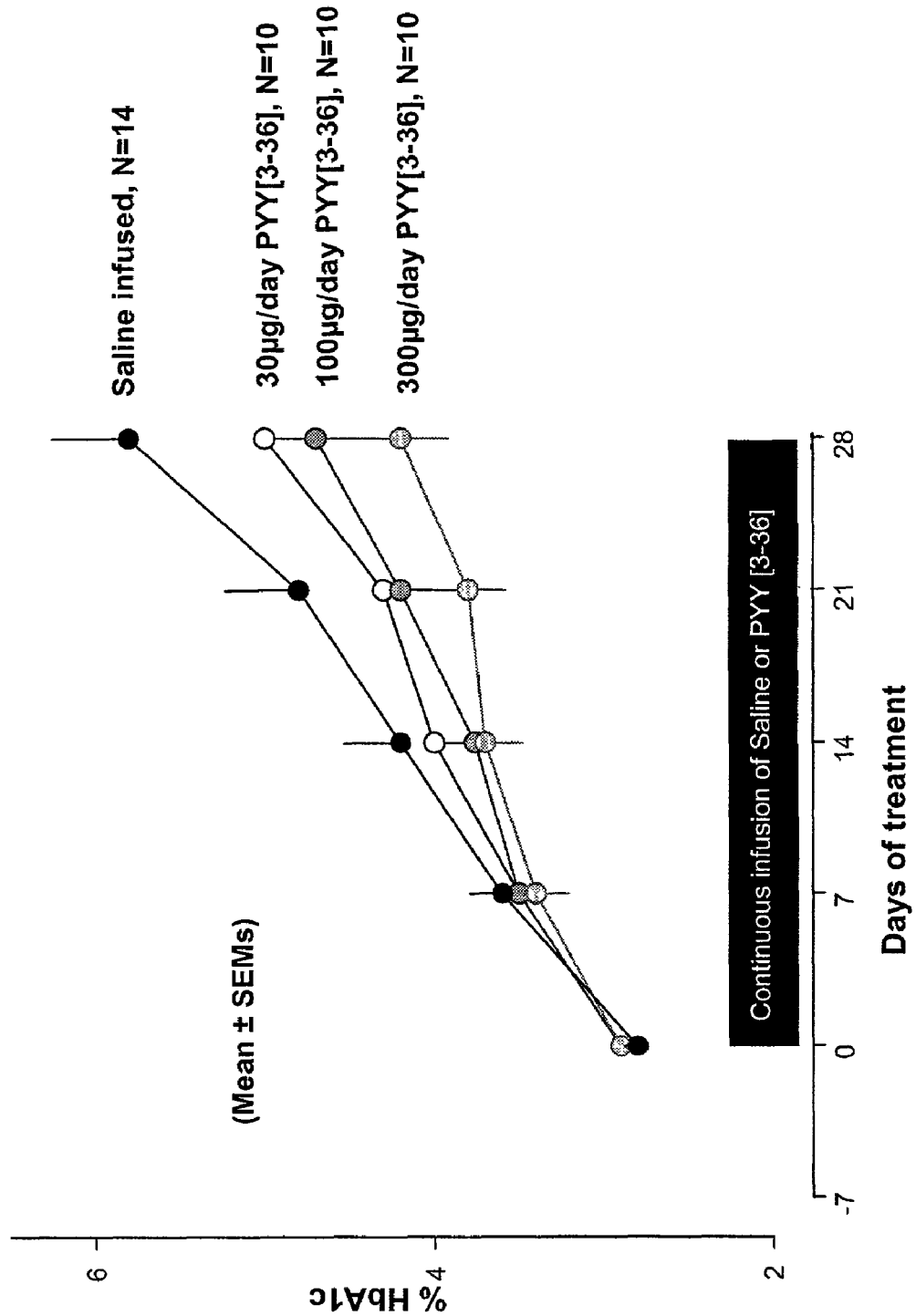
FIG. 8 demonstrates the improvement in glycemic control as measured by percent change in HbA1c over a period of 28 days in obese diabetic (ZDF) rats upon continuous peripheral infusion of PYY[3-36].

Animals were implanted with osmotic pumps which delivered the doses indicated in FIG. 8 of PYY[3-36] or saline continuously to the periphery for 28 days. HbA1c was measured at weekly intervals. HbA1c levels (%) were plotted against time (Brown, Henke et al. *Diabetes* 48: 1415-24, 1999).

Results:

As indicated in FIG. 8, PYY[3-36] administered continuously by peripheral infusion to Diabetic Zucker Fatty (ZDF) rats produced a dose-dependent improvement in long term blood glucose control as measured by the level of HbA1c. The improvement in glycemic control increased throughout the treatment period, and was significant at all doses of PYY[3-36] at 28 days.

The above Examples directly indicate that PYY agonists have utility in reducing caloric availability, and can be used as therapeutics to treat conditions that benefit from reduced caloric availability, such as obesity and type 2 diabetes. Further, the Examples indicate that the effects of PYY agonists to reduce caloric availability could occur through several mechanisms, and provide a framework to identify a PYY agonist. Since PYY and NPY are reported to be equipotent and equally effective in all Y1 and Y2 receptor assays studied, the data in Examples 1 and 2 above indicate that the effects of PYY and agonists on reducing food intake (FIG. 1) and delaying gastric emptying (FIG. 2) are not mediated through Y1 or Y2 receptors. Those data show that PYY's effects on food intake and gastric emptying are not comparable to reported effects on Y1 and Y2 receptors, since NPY showed little or no activity in these assays.

FIG. 1 illustrates one aspect of the invention. It is known that central administration of a PYY or NPY agonist increases food intake (Clark, Kalra et al. *Endocrinology* 115: 427-9, 1984; Clark, Sahu et al. *Regul Pept* 17: 31-9, 1987). Surprisingly, we have found that peripheral administration of PYY or PYY[3-36] effectively decreases food intake. Not presented here, we have documented that PYY[3-36] reduced food intake in long term studies in other rodent models including the ob/ob mouse, and fa/fa rat. Administered peripherally, other members of the PP family have little or no effect on food intake. The order of potency, and in particular, the lack of effect of NPY, does not reflect the pharmacology of any of the known cloned Y receptors. The unique pharmacology of PYY agonists is further established by their potent effect to delay gastric emptying compared with other PP family members which are inactive in this assay (see, e.g., data in FIG. 2).

Characterization of the PYY agonist PYY[3-36] illustrates additional mechanisms that could reduce caloric availability. These include decreased gastric acid secretion (FIG. 3), decreased exocrine pancreatic secretion (FIG. 5), and delayed gallbladder emptying (FIG. 4). Without being bound by any theory, we hypothesize that this entire spectrum of effects on food intake and gastrointestinal function contributes to the utility of PYY agonists to decrease caloric availability. For example, PYY and PYY[3-36] reportedly inhibited vagally stimulated gastric acid output in rabbits (Lloyd, Grandt et al. *Am J Physiol* 270: G123-G127, 1996). PYY also inhibited pentagstrin-stimulated gastric acid secretion in humans (Adrian, Ferri et al. *Gastroenterology* 89: 1070-7, 1985) and rats (Greeley, Guo et al. *Proc Soc Exp Biol Med* 189: 325-8, 1988), and CRF-induced gastric-acid secretion in rats (Gue, Junien et al. *Br J Pharmacol* 118: 237-42, 1996). PYY (Yoshinaga, Mochizuki et al *Am J Physiol* 263: G695-701, 1992) (Guan, Maouyo, et al. *Endocrinology* 128: 911-6, 1991) (Pappas, Debas et al. *Am J Physiol* 248: G118-23, 1985) and PYY[3-36] (Deng, Guarita et al. *Dig Dis Sci* 46: 156-65, 2001) have also been reported to inhibit pancreatic enzyme secretion. In normal humans, PYY was recently reported to reduce the cephalic, but not the CCK-dependent phase of gallbladder emptying (Hoentjen, Hopman et al. *Scand J Gastroenterol* 35: 166-71, 2000).

We propose that treatment with a PYY agonist via mechanisms identified herein will decrease body weight. We have established, in several obese rodent models, that peripheral administration of PYY[3-36] produces a dose-dependent decrease in body weight and/or rate of weight gain. We demonstrate the effect herein in a diet-induced obese (DIO) mouse model (FIG. 6).

Additionally, as summarized in FIG. 1, peripheral administration of a PYY agonist decreases food intake. From a calculation of the body weight gained per kcal consumed in the DIO mouse study, it is clear that peripheral administration of a PYY agonist decreases the efficiency with which calories are converted into body mass (FIG. 7). Thus, the present Examples support an effect of PYY agonists to reduce body weight gain in association with reduced caloric availability.

PYY and PYY agonists in particular have utility in the treatment of diseases that will benefit from reduced caloric availability such as obesity, type 2 diabetes and cardiovascular disease. We have examined the antidiabetic activities of PYY[3-36] in an obese diabetic rodent, the ZDF rat. Peripheral administration of the PYY agonist produces a significant, robust and dose-related improvement in glycemic control as measured by hemoglobin A1c levels (FIG. 8). While not presented in the Example, food intake was also reduced by PYY[3-36] administration.

Example 9

Area Postrema Assay

Peripherally administered PYY has been reported to activate neurons in the area postrema (Bonaz, Taylor et al. *Neurosci Lett* 163: 77-80, 1993). Evaluation of the PYY agonist activity of potential compounds of the invention can be carried out using the area postrema assay as follows, in combination with an assay of PYY effect, for example those of Examples 1 and 2.

Membrane Preparation

In this assay, area postrema membranes were prepared from tissue dissected from the pig or bovine brain stem. Area postrema membrane preparations are initiated by brief (4-10 seconds) homogenization of tissues using, e.g., a Polytron tissue homogenizer (Brinkman Instruments, NY) at ice-cold temperatures in a buffered solution such as phosphate buffered saline (138 nM NaCl, 8.1 M $Na_2PO_4$, 2.5 M KCl, 1.2 M $KH_2PO_4$, 0.9 M $CaCl_2$, 0.5 mM $MgCl_2$, pH 7.4). Following tissue disruption, large particles and debris were cleared by centrifugation (200×g, 5 minutes, 4° C.) and the supernatant fraction is reserved on ice. Membranes are isolated from the supernatant fraction by high-speed centrifugation (at least 40,000×g, for at least 10 minutes, 4° C.). Membranes are normally washed at least twice by re-homogenization in fresh buffer and recentrifugation, in order to remove endogenous interfering substances. Washed membranes are resuspended in buffer containing a proteolytic enzyme inhibitors such as phenylmethylsulfonyl fluoride (PMSF) or bacitracin. Volumes of buffer may be added sufficient to adjust the final tissue concentration to a level suitable for the particular screening method employed.

Binding Reactions

In one embodiment, incubation mixtures for the screening method are set up as follows. To glass or polymeric tubes are added a small volume of Buffer Mixture ("HBBM") composed of a buffer solution such as HEPES containing a protease inhibitor such as bacitracin or PMSF, protease-free serum albumin (preferable fraction V BSA, protease-free) and, optionally, a $Mg^{2+}$ or $Ca^{2+}$ salt, and EDTA. To the Buffer Mixture is added a small volume of buffer containing the unlabeled molecules to be tested for agonist activity at concentrations of about from $10^{-11}$ to $10^{-6}$ M. Control tubes contain buffer alone. To this mixture is added amounts of labeled area postrema preparation ligand (here, PYY), in buffer so as to produce final concentrations of from about 10 to about 100 pM. Because of the high specific activities obtainable and ease of chemical labeling, $^{125}I$ is preferred to label the area postrema ligands. Ligands may be isolated from human tissues, from animal tissues, or produced by chemical, synthetic, or recombinant means. Labeled area postrema preparation ligands are dissolved in sterile water containing protease-free Fraction V BSA, aliquoted, and stored frozen until use.

Reactions are begun by adding, for example, membranes to each incubation tube. The amount of membrane protein required per tube is varied so that the amount of labeled ligand bound by the membranes in the assay is less than, for example, 10% of the total concentration of ligand in the assay (typically about 100 µg).

Reaction mixtures are incubated for a period of time and at a temperature sufficient to reach steady-state conditions within the period. The term "steady state" as used herein is intended to encompass the sum total of all reactions and processes that influence the net amount of bound hormone. It may or may not be synonymous with "equilibrium." Typically, tubes are incubated for about 60 minutes at room temperature.

Detection

When membranes are used, they are isolated following binding in order to determine the amount of labeled ligand bound after competition between labeled and unlabeled ligands. It is convenient to collect membranes by filtration with a vacuum-powered Brandel Cell Harvester (Brandel Instruments, Gaithersburg, Md., Model M-24) through glass fiber filters (e.g., GF/B, Whatman) that have been presoaked with a regent in order to reduce nonspecific binding (NSB). Preferred is presoaking filters for about 5 hours in about 0.3% polyethyleneimine. The skilled artisan will know of other membrane collecting devices, such as the Millipore Filtration Assembly ((Model 1225) or the Sandbeck filter box (Bennett, J. P., in *Neurotransmitter Receptor Binding*, H. I. Yamura, et al., Raven, N.Y. 1978, Pages 57-90), collecting filters, and NSB-reducing reagents that can be used in receptor binding assays. Both immediately before and immediately after filtration, filters are washed with large (milliliter) volumes of ice cold buffer to remove contaminating materials, e.g., unbound labeled ligand. Filters are removed and the amount of labeled ligand bound to membranes is quantified. Where $^{125}I$ is the label, radioactivity may be assessed in a gamma ray counter. Where a chemiluminescent reporter molecule (e.g., AMPPD, Tropix, Inc., Bedford, Mass.) is used, the light produced may be quantified in a luminometer. Enzymatic and fluorescent labels may also be used.

Instead of by filtration, membranes may be isolated following incubation by centrifugation (e.g., Beckman-2-21-M refrigerated centrifuge at 21,000 rpm or a Beckman 12 or Eppendorf microfuge), washed with ice cold buffer, then counted as such or following solubilization of membranes by detergent or alkali.

Data Analysis

Scatchard plot saturation analyses of binding data, wherein bound/free (B/F) labeled ligand is plotted as a function of the amount bound, are performed by standard methods. See, e.g., (Scatchard. *Ann NY Acad Sci* 51: 660, 1949).

Competition curves, wherein the amount bound (B) is plotted as a function of the log of the concentration of ligand may be analyzed by computer, e.g., analyses by nonlinear regression to a 4-parameter logistic equation (Prism Program; GraphPAD Software, San Diego, Calif.) or the ALLFIT program (Version 2.7 (NIH, Bethesda, Md. 20892)) (Munson and Rodbard. *Anal Biochem* 107: 220-39, 1980; de Lean, A., Munson, P. J. et al. 1988).

To determine binding constants, Scatchard saturation curves may be generated and analyzed according to a modification of the method of Scatchard, as described by Bylund, D. B., et al., "Methods for Receptor Binding," In H. I. Yamamura et al., eds., *Methods in Neurotransmitter Analysis*, Raven Press, New York, 1990 pp. 1-35.

In order to obtain specific binding values experimentally, a broad range of tracer concentrations of labeled ligand (typically, 1-150 pM) is used to obtain total binding and duplicate tubes reassessed, in the presence of a very high concentration, e.g., 100 nM, of unlabeled ligand, to obtain nonspecific binding (NSM). The latter value is subtracted from each total binding value in order to obtain specific binding at every concentration of labeled ligand.

Example 10

Y Receptor Binding Assay

Evaluation of the PYY agonist activity of potential compounds of the invention can be carried out by investigating their interaction with any of the known Y receptors, such as Y1-Y6, or with one or more unique receptor classes similar to the PYY-preferring receptors (such as Y7) expressed in cells, in combination with an assay of PYY effect, for example those of Examples 1 and 2. These cells may endogenously express the Y receptor of interest (such as SK-N-MC cells that express Y1 receptors or SK-N-BE2 cells which express Y2 receptors) or may be other cells (such as COS-7 or HEK293 cells) that are transfected with the clone of the Y receptor of interest. Binding to SK-N-BE2 cells is used as an example.

Cell Culture

SK-N-BE2 cells are grown on, for example 150 mm plates in tissue culture medium with supplements (Dulbecco's Modified Eagle Medium with 10% fetal calf serum, 4 nM glutamine, 100 units/mL penicillin and 100 µmg/mL streptomycin) at 37° C. in 5% $CO_2$ humidified atmosphere. Stock plates are trypsinized and split 1:6 every 3-4 days.

Membrane Preparation

Cells are scraped from the plates in a small volume of a buffered solution such as phosphate buffered saline (138 mM NaCl, 8.1 mM $Na_2PO_4$, 2.5 mM KCl, 1.2 mM $KH_2PO_4$, 0.9 mM CaCl$_2$, 0.5 mM MgCl$_2$, pH 7.4), or are trypsinized, washed and resuspended in buffered solution. Membrane preparations are initiated by brief (10 seconds) homogenization of cells using, e.g., a Polytron tissue homogenizer (Brinkman Instruments, NY) at ice-cold temperatures. Membranes are further prepared by centrifugation as described above in Example 9. Binding reactions, detection and data analysis are as described in Example 9.

Various modifications of the invention in addition to those shown and described herein will be apparent to those skilled in the art from the foregoing description and fall within the scope of the following claims.

We claim:

1. A method of reducing food intake comprising peripherally administering to a human subject, via a parenteral route, an amount of PYY agonist analog effective to reduce food intake, wherein the PYY agonist analog is PYY[3-36], and wherein the amount is in the range of about 100 μg/kg to 1,000 μg/kg per day in a single or divided dose.

2. A method of reducing body weight or reducing body weight gain comprising peripherally administering to a subject having obesity an amount of PYY[3-36], wherein the amount is in the range of about 300 μg/kg to 1,000 μg/kg per day in a single or divided dose.

3. A method of reducing food intake and body weight comprising peripherally administering to a subject having obesity an amount of PYY[3-36], wherein the amount is in the range of about 300 μg/kg to 1,000 μg/kg per day in a single or divided dose.

4. A method of treating obesity comprising peripherally administering to a subject an amount of PYY[3-36], wherein the amount is in the range of about 300 μg/kg to 1,000 μg/kg per day in a single or divided dose.

5. The method according any one of claims 1 and 2-4, further comprising administration of a GLP-1, an exendin, an amylin, a leptin, their agonists, or any combination thereof.

6. The method according to any one of claims 1 and 2-4, wherein PYY[3-36] is administered by an intravenous, intraperitoneal, intramuscular, subcutaneous, topical, nasal or pulmonary inhalation route of administration.

7. The method of any one of claims 2-4, wherein the subject is a human.

* * * * *

UNITED STATES PATENT AND TRADEMARK OFFICE
CERTIFICATE OF CORRECTION

PATENT NO. : 8,273,713 B2  Page 1 of 1
APPLICATION NO. : 10/016969
DATED : September 25, 2012
INVENTOR(S) : Pittner et al.

It is certified that error appears in the above-identified patent and that said Letters Patent is hereby corrected as shown below:

Title Page 2, Right Column, Item (56) OTHER PUBLICATIONS:
 Line 53, before "1996." delete "(poster p2-58)" and insert --(poster P2-58)--

Title Page 3, Left Column, Item (56) OTHER PUBLICATIONS:
 Line 18, before "1989" delete "Neuropsycholiology" and insert --Neuropsychology--

Title Page 4, Left Column, Item (56) OTHER PUBLICATIONS:
 Line 3, delete "hyperlipoproteinaemia" and insert --hyperlipoproteinemia-- therefor
 Line 21, delete "effecto" and insert --effect of-- therefor
 Line 24, delete "empyting" and insert --emptying-- therefor
 Line 42, delete "antagonis" and insert --antagonist-- therefor Title Page 5, Right Column, Item (56) OTHER PUBLICATIONS:
 Line 14, delete "phan-nacokinetics, or phartriacociyriamics" and insert --pharmacokinetics or pharmacodynamics-- therefor
 Line 18, delete "brain-got" and insert --brain-gut-- therefor
 Line 19, delete "Ravimwo8:55-G9" and insert --Reviews 8:55-69-- therefor In the Claims Column 24, line 29, after "according" insert --to--

Signed and Sealed this
Third Day of December, 2013

Margaret A. Focarino
*Commissioner for Patents of the United States Patent and Trademark Office*

SEQUENCE LISTING

```
<160> NUMBER OF SEQ ID NOS: 6

<210> SEQ ID NO 1
<211> LENGTH: 36
<212> TYPE: PRT
<213> ORGANISM: Homo sapiens

<400> SEQUENCE: 1

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 2
<211> LENGTH: 36
<212> TYPE: PRT
<213> ORGANISM: Homo sapiens

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 34
<212> TYPE: PRT
<213> ORGANISM: Homo sapiens

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 4
<211> LENGTH: 36
<212> TYPE: PRT
<213> ORGANISM: Homo sapiens

<400> SEQUENCE: 4

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35
```

```
<210> SEQ ID NO 5
<211> LENGTH: 34
<212> TYPE: PRT
<213> ORGANISM: Homo sapiens

<400> SEQUENCE: 5

Ser Lys Pro Asp Asn Pro Gly Glu Asp Ala Pro Ala Glu Asp Met Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 6
<211> LENGTH: 15
<212> TYPE: PRT
<213> ORGANISM: Homo sapiens

<400> SEQUENCE: 6

Ala Ser Leu Arg His Tyr Leu Asn Leu Val Thr Arg Gln Arg Tyr
1               5                   10                  15
```